(12) United States Patent
Ting et al.

(10) Patent No.: US 12,083,193 B2
(45) Date of Patent: *Sep. 10, 2024

(54) ANTI-HER2 NANOBODY AND CODING SEQUENCE AND USE THEREOF

(71) Applicant: NANOMAB TECHNOLOGY LIMITED, Central (HK)

(72) Inventors: Hong Hoi Ting, Shanghai (CN); Chung Lim Wong, Shanghai (CN); Wenhua Huang, Shanghai (CN)

(73) Assignee: NANOMAB TECHNOLOGY LIMITED, Central (HK)

( * ) Notice: Subject to any disclaimer, the term of this patent is extended or adjusted under 35 U.S.C. 154(b) by 9 days.

This patent is subject to a terminal disclaimer.

(21) Appl. No.: 18/047,327

(22) Filed: Oct. 18, 2022

(65) Prior Publication Data
US 2023/0263916 A1    Aug. 24, 2023

Related U.S. Application Data

(63) Continuation of application No. 16/624,403, filed as application No. PCT/CN2018/091953 on Jun. 20, 2018, now Pat. No. 11,517,632.

(30) Foreign Application Priority Data

Jun. 20, 2017  (CN) .......................... 201710471319.6

(51) Int. Cl.
*A61K 51/10* (2006.01)
*A61K 47/68* (2017.01)
*C07K 16/32* (2006.01)

(52) U.S. Cl.
CPC ...... *A61K 51/1051* (2013.01); *A61K 47/6803* (2017.08); *A61K 47/6855* (2017.08);
(Continued)

(58) Field of Classification Search
CPC ............ A61K 51/1051; A61K 47/6803; A61K 47/6855; C07K 16/32; C07K 2317/51; C07K 2317/92
See application file for complete search history.

(56) References Cited

U.S. PATENT DOCUMENTS

| 11,517,632 B2 | 12/2022 | Ting et al. |
| 2016/0144062 A1 | 5/2016 | Hiscock et al. |
| 2017/0066830 A1* | 3/2017 | Bodyak ................ A61K 45/06 |

FOREIGN PATENT DOCUMENTS

| CN | 106866823 A | 6/2017 |
| CN | 107236046 A | 10/2017 |

(Continued)

OTHER PUBLICATIONS

Chan, P., et al (2008) Engineering a camelid antibody fragment that binds to the active site of human lysozyme and inhibits its conversion into amyloid fibrils Biochemistry 47; 11041-11054 (Year: 2008).*

(Continued)

*Primary Examiner* — Scarlett Y Goon
*Assistant Examiner* — Audrey L Buttice
(74) *Attorney, Agent, or Firm* — McCarter & English, LLP; Marcie B. Clarke

(57) ABSTRACT

Provided are an anti-Her2 nanobody and a coding sequence and the use thereof. In particular, provided is a nanobody combating human epidermal growth factor receptor-2 (Her2/ERBB2). Disclosed are the nanobody and the a gene sequence encoding the nanobody, a corresponding expression vector and a host cell capable of expressing the nanobody, and a method for producing the nanobody of the present invention and the related use thereof. The present invention may also provide an immunoconjugate of the (Continued)

nanobody and the use thereof, especially the use in the diagnosis and treatment of Her2 positive tumor.

12 Claims, 3 Drawing Sheets

Specification includes a Sequence Listing.

(52) U.S. Cl.
 CPC ......... C07K 16/32 (2013.01); *C07K 2317/51* (2013.01); *C07K 2317/92* (2013.01)

(56) References Cited

FOREIGN PATENT DOCUMENTS

| CN | 112500480 A | 3/2021 |
| WO | 2009/068625 A2 | 6/2009 |
| WO | 2016/016329 A1 | 2/2016 |
| WO | 2017/101828 A1 | 6/2017 |

OTHER PUBLICATIONS

Chopra, [99m Tc] Epidermal growth factor receptor-specific nanobody. Molecular Imaging and Contrast Agent Database (MICAD) [Internet]. May 13, 2008. 5 pages.

International Search Report and Written Opinion for Application No. PCT/CN2018/091953, dated Aug. 21, 2018, 14 pages.

* cited by examiner

Nanobody | 20x nanobody inhibition | 20x Trastuzumab inhibition | 20xPatozumab inhibition

SEQUENCE LISTING

```
Sequence total quantity: 80
SEQ ID NO: 1            moltype = AA  length = 123
FEATURE                 Location/Qualifiers
source                  1..123
                        mol_type = protein
                        organism = Camelus bactrianus
SEQUENCE: 1
QVQLQESGGG SVQAGETLRL SCTASGFTFD DSDMGWYRQA PGNECELVST ISSDGSTYYA  60
DSVKGRFTIS QDNAKNTVYL QMNSLKPEDT AVYYCAAHPL HYELGTCAAL DYWGRGTQVT  120
VSS                                                                123

SEQ ID NO: 2            moltype = AA  length = 123
FEATURE                 Location/Qualifiers
source                  1..123
                        mol_type = protein
                        organism = Camelus bactrianus
SEQUENCE: 2
QVQLQESGGG SVQAGETLRL SCTASGFTFD DSDMGWYRQA PGNECELVST ISSDGSTYYA  60
DSVKGRFTIS QDNAKNAVYL QMNSLKPEDT AVYYCAAHPL HYELGTCAAL DYWGRGTQVT  120
VSS                                                                123
```

```
SEQ ID NO: 3               moltype = AA   length = 123
FEATURE                    Location/Qualifiers
source                     1..123
                           mol_type = protein
                           organism = Camelus bactrianus
SEQUENCE: 3
QVQLQESGGG SVQAGGSLRL SCTASGFTFD DSDVRWYRQA PGRECKLVSS ISSDRSAYYE   60
DSVKGRFTIS QDNAKNTVYL QMNSLKPEDT AVYYCAAHPL HYELGTCAAL DYWGRGTQVT  120
VSS                                                                123

SEQ ID NO: 4               moltype = AA   length = 123
FEATURE                    Location/Qualifiers
source                     1..123
                           mol_type = protein
                           organism = Camelus bactrianus
SEQUENCE: 4
QVQLQESGGG LVQPGGSLRL SCTASRFTFD DSDMAWYRQA PGNECELVSI ISSDGSTYYA   60
DSVKGRFTIS LDNTKSTVYL QMNSLKPEDT AVYYCAAHPL HYELGTCAAL DYWGRGTQVT  120
VSS                                                                123

SEQ ID NO: 5               moltype = AA   length = 118
FEATURE                    Location/Qualifiers
source                     1..118
                           mol_type = protein
                           organism = Camelus bactrianus
SEQUENCE: 5
QVQLQESGGG SVQAGGSLRL SCTVSGFSFD DSDMGWYRRA PGNECELVSG ISRDGSTYYA   60
DSVKGRFTIS QDNAKNWVYL QMNSLKPEDT AVYYCAAATY SDYVCDYWTQ GTQVTVSS    118

SEQ ID NO: 6               moltype = AA   length = 125
FEATURE                    Location/Qualifiers
source                     1..125
                           mol_type = protein
                           organism = Camelus bactrianus
SEQUENCE: 6
QVQLQESGGG SVQAGETLRL SCTASGFTFD DSDMGWYRQA PGNECELVSH ISSDGSTYYA   60
DSVKGRFTIS QDNAKNTVFL QMNSLKPEDT AVYYCAADKD ARGYELGTCE SLDYWGRGTQ  120
VTVSS                                                              125

SEQ ID NO: 7               moltype = AA   length = 125
FEATURE                    Location/Qualifiers
source                     1..125
                           mol_type = protein
                           organism = Camelus bactrianus
SEQUENCE: 7
QVQLQESGGG SVQAGETLRL SCTASGFTFD DSDMGWYRQA PGNECELVST ISSDGSTYYA   60
DSVKGRFTIS QDNAKNTVYL QMNSLKPEDT AVYYCAADKD ARGYELGTCE SLDYWGRGTQ  120
VTVSS                                                              125

SEQ ID NO: 8               moltype = AA   length = 123
FEATURE                    Location/Qualifiers
source                     1..123
                           mol_type = protein
                           organism = Camelus bactrianus
SEQUENCE: 8
QVQLQESGGG SVQAGETLRL SCTASGFTFD ESVMGWYRQA PGNECELVST ISSDGSTYYS   60
NSVKGRFTIS QDNAKNTVYL QMNSLKPEDT AVYYCAADDH TYELGTCEAL NYWGRGTQVT  120
VSS                                                                123

SEQ ID NO: 9               moltype = AA   length = 123
FEATURE                    Location/Qualifiers
source                     1..123
                           mol_type = protein
                           organism = Camelus bactrianus
SEQUENCE: 9
QVQLQESGGG SVQAGETLRL SCTASGFTFD DSDMGWYRQA PGSECELVST ISSDGNTYYS   60
NSVKGRFTIS QDNAKNTVYL QMNSLKPEDT AVYYCAADDQ HYELGTCEAL DYWGRGTQVT  120
VSS                                                                123

SEQ ID NO: 10              moltype = AA   length = 123
FEATURE                    Location/Qualifiers
source                     1..123
                           mol_type = protein
                           organism = Camelus bactrianus
SEQUENCE: 10
QVQLQESGGG SVQAGETLKL SCTASGFTFD DSTMAWYRQA PGNECKLVST ISSDGSTYYA   60
DSVKGRFTIS QDNAKNTVYL QMNSLKPEDT AVYYCAADDQ NYELGTCEAL DYWGRGTQVT  120
VSS                                                                123
```

```
SEQ ID NO: 11          moltype = AA  length = 123
FEATURE                Location/Qualifiers
source                 1..123
                       mol_type = protein
                       organism = Camelus bactrianus
SEQUENCE: 11
QVQLQESGGG SVQAGETLRL SCTASGFTFD DSDMGWYRQA PGNECELVSH ISSGGSTYYA    60
DSVKGRFTIS QDNAKNTVYL QMNSLKPEDT AVYYCAADGS NYELGTCAAL DYWGRGTQVT   120
VSS                                                                 123

SEQ ID NO: 12          moltype = AA  length = 123
FEATURE                Location/Qualifiers
source                 1..123
                       mol_type = protein
                       organism = Camelus bactrianus
SEQUENCE: 12
QVQLQESGGG SVQAGETLRL SCTASGFTFD DSDMGWYRQA PGNECELVST ISSDGSTYYA    60
DSVKGRFTIS QDNAKNTVYL QMNSLKPEDT AVYYCAADGH KYELGTCAAL DYWGRGTQVT   120
VSS                                                                 123

SEQ ID NO: 13          moltype = AA  length = 123
FEATURE                Location/Qualifiers
source                 1..123
                       mol_type = protein
                       organism = Camelus bactrianus
SEQUENCE: 13
QVQLQESGGG SVQAGETLRL SCTASGFTFD DSDMGWYRQA PGNECELVST ISADGSTFYA    60
DSVKGRFTIS QDNAKNTVYL QMNSLKPEDT AVYYCASPEN EYELGTCEAL DYWGQGTQVT   120
VSS                                                                 123

SEQ ID NO: 14          moltype = AA  length = 123
FEATURE                Location/Qualifiers
source                 1..123
                       mol_type = protein
                       organism = Camelus bactrianus
SEQUENCE: 14
QVQLQESGGG SVQAGETLRL SCTASGFTFD DSDMGWYRQA PGNECELVSR ISSDGSTYYA    60
DSVKGRFTIS QDNAKNTVYL QMNSLKPEDT AVYYCAALEW EYELGTCEAL DYWGQGTQVT   120
VSS                                                                 123

SEQ ID NO: 15          moltype = AA  length = 123
FEATURE                Location/Qualifiers
source                 1..123
                       mol_type = protein
                       organism = Camelus bactrianus
SEQUENCE: 15
QVQLQESGGG SVQAGGSLRL SCTASRFTFD DSDMGWYRQA PGNECELVST ISSDGATYYA    60
NSVKGRFTIS QDNAANTVYL QMNSLKPEDT AVYYCAALEW EYELGTCEAL DYWGQGTQVT   120
VSS                                                                 123

SEQ ID NO: 16          moltype = AA  length = 123
FEATURE                Location/Qualifiers
source                 1..123
                       mol_type = protein
                       organism = Camelus bactrianus
SEQUENCE: 16
QVQLQESGGG SVQAGGSLRL SCTASGFTFD DSDMVWYRQA PGNECELVSR ISSDGSTYYA    60
DSVKGRFTIS QDNAKNTVYL QMNSLKPEDT AVYYCAALEW EYELGTCEAL DYWGQGTQVT   120
VSS                                                                 123

SEQ ID NO: 17          moltype = AA  length = 123
FEATURE                Location/Qualifiers
source                 1..123
                       mol_type = protein
                       organism = Camelus bactrianus
SEQUENCE: 17
QVQLQESGGG SVQAGGSLRL SCTASGFTFD DSDMGWYRQA PGNECELVST ISSDGSTYYA    60
DSVKGRFTIS QDNAKNTVYL QMNSLKPEDT AVYYCADVQI PYGLGTCESL DYWGRGTQVT   120
VSS                                                                 123

SEQ ID NO: 18          moltype = AA  length = 122
FEATURE                Location/Qualifiers
source                 1..122
                       mol_type = protein
                       organism = Camelus bactrianus
SEQUENCE: 18
QVQLQESGGG SVQAGQTLRL SCTASGFTFD DSDMAWYRQA PGNECELVSK MRSDGSTYYA    60
DSVKGRFTIS QDNAKNTVYL QMNSLKPEDT AVYYCAEDLP YGLGTCTSLD YWGRGTQVTV   120
```

```
SS                                                                                      122

SEQ ID NO: 19              moltype = AA   length = 125
FEATURE                    Location/Qualifiers
source                     1..125
                           mol_type = protein
                           organism = Camelus bactrianus
SEQUENCE: 19
QVQLQESGGG SVQAGGSLRL SCTASGFTFD DSDSDMGWYR QAPGNECELV SSISSDGSTY        60
YADSVKGRFT ISQDNAKNTV YLQMNSLKPE DTAVYYCAAI NSGYELGTCE SLDYWGRGTQ       120
VTVSS                                                                  125

SEQ ID NO: 20              moltype = AA   length = 123
FEATURE                    Location/Qualifiers
source                     1..123
                           mol_type = protein
                           organism = Camelus bactrianus
SEQUENCE: 20
QVQLQESGGG SVQAGGSLRL SCTASGFTFD DSVMGWFRKA PGNECELVST ISSDGSTYYA        60
DSVKGRFTIS QDNAKNTVYL QMNNLKPEDT AVYYCAAINS GYELGTCESL DYWGRGTQVT       120
VSS                                                                    123

SEQ ID NO: 21              moltype = AA   length = 125
FEATURE                    Location/Qualifiers
source                     1..125
                           mol_type = protein
                           organism = Camelus bactrianus
SEQUENCE: 21
QVQLQESGGG LVQPRGSLRL SCTASGFTFD DSDSDMGWYR QAPGNECELV SSISSDGSTY        60
YADSVKGRFT ISQDNAKNTV YLQMNSLKPE DTAVYYCAAI NSGYELGTCE SLDYWGRGTQ       120
VTVSS                                                                  125

SEQ ID NO: 22              moltype = AA   length = 123
FEATURE                    Location/Qualifiers
source                     1..123
                           mol_type = protein
                           organism = Camelus bactrianus
SEQUENCE: 22
QVQLQESGGG SVQAGGSLRL SCTASGFTFD DSDMGWYRQA PGNECELVSR ISRDGTTYYA        60
DSVKGRFTIS QDNAKNTVYL QMNSLKPEDT AVYYCADINS GYELGTCESL DYWGRGTQVT       120
VSS                                                                    123

SEQ ID NO: 23              moltype = AA   length = 123
FEATURE                    Location/Qualifiers
source                     1..123
                           mol_type = protein
                           organism = Camelus bactrianus
SEQUENCE: 23
QVQLQESGGG SVQAGGSLKL SCSASGFTFD DTDMGWYRQA PGNECELVST ISSDGTTYYT        60
DSVKGRFTIS QDNAKNTVYL QMNSLKPEDT AVYYCAAINS GYELGTCESL DYWGRGTQVT       120
VSS                                                                    123

SEQ ID NO: 24              moltype = AA   length = 125
FEATURE                    Location/Qualifiers
source                     1..125
                           mol_type = protein
                           organism = Camelus bactrianus
SEQUENCE: 24
QVQLQESGGG SVQAGETLRL SCTASGFTFD DSDSDMGWYR QAPGNECELV SSISSDGSTY        60
YADSVKGRFT ISQDNAKNTV YLQMNSLKPE DTAVYYCAAI NSGYELGTCE SLDYWGRGTQ       120
VTVSS                                                                  125

SEQ ID NO: 25              moltype = AA   length = 125
FEATURE                    Location/Qualifiers
source                     1..125
                           mol_type = protein
                           organism = Camelus bactrianus
SEQUENCE: 25
QVQLQESGGG SVQAGETLRL SCTASGFTFD DSDSDMGWYR QAPGNECELV SSISSDGSTY        60
YADSVKGRFT ISQDNAKNTV YLQMNSPKPE DTAVYYCAAI NSGYELGTCE SLDYWGRGTQ       120
VTVSS                                                                  125

SEQ ID NO: 26              moltype = AA   length = 123
FEATURE                    Location/Qualifiers
source                     1..123
                           mol_type = protein
                           organism = Camelus bactrianus
SEQUENCE: 26
QVQLQESGGG SVQAGETLRL SCTASGFTFD DSDMGWYRQA PGNECELVSS ISSDGSTYYA        60
```

```
DSVKGRFTIS QDNAKNTVYL QMNSLKPEDT GVYYCAAEGH RYELGTCAAL DYWGRGTQVT   120
VSS                                                                123

SEQ ID NO: 27           moltype = AA  length = 124
FEATURE                 Location/Qualifiers
source                  1..124
                        mol_type = protein
                        organism = Camelus bactrianus
SEQUENCE: 27
QVQLQESGGG SVQAGETLRL SCTASGFTFD DSDMGWYRQA PGNECELVST ISSDGSTYYA   60
DSVKGRFTIS QDNAKNTVYL QMNSLKPEDT AVYYCAADHG GGYELGTCAA LDYWGRGTQV   120
TVSS                                                               124

SEQ ID NO: 28           moltype = AA  length = 123
FEATURE                 Location/Qualifiers
source                  1..123
                        mol_type = protein
                        organism = Camelus bactrianus
SEQUENCE: 28
QVQLQESGGG LVQPGGSLRL SCAASGFTFG DSGMGWYRQA PGNECELVSS VSSDGSTYYA   60
DSVKGRFTIS QDNAKNTVYL RMNSLKPEDT AVYYCAADDH KYELGTCEAL DYWGRGTQVT   120
VSS                                                                123

SEQ ID NO: 29           moltype = AA  length = 123
FEATURE                 Location/Qualifiers
source                  1..123
                        mol_type = protein
                        organism = Camelus bactrianus
SEQUENCE: 29
QVQLQESGGG SVQAGGSLRL SCTASGFTFD DLDMRWYRQA PGNECELVSI INSDGRTYYA   60
DSVKGRFAIS QNNAKNTVYL QMNSLKPEDT AVYYCAADQH RYGLGTCEAL DYWGRGTQVT   120
VSS                                                                123

SEQ ID NO: 30           moltype = AA  length = 123
FEATURE                 Location/Qualifiers
source                  1..123
                        mol_type = protein
                        organism = Camelus bactrianus
SEQUENCE: 30
QVQLQESGGG SVQAGETLRL SCTASGFTFD DSDMGWYRQA PGNECELVST ISSDGRTYYA   60
DSVKGRFAIS QNNAKNTVYL QMNSLKPEDT AVYYCAADQH RYGLGTCEAL DYWGRGTQVT   120
VSS                                                                123

SEQ ID NO: 31           moltype = AA  length = 122
FEATURE                 Location/Qualifiers
source                  1..122
                        mol_type = protein
                        organism = Camelus bactrianus
SEQUENCE: 31
QVQLQESGGG SVQAGETLRL SCTASGFTFN DSNMGWYRQA PGHECELVST ISSDGSTYYA   60
DSVKGRFTIS QNNARNTVYL QMNSLKPEDT AVYYCAGDWG YELGICTSLD YWGQGTQVTV   120
SS                                                                 122

SEQ ID NO: 32           moltype = AA  length = 120
FEATURE                 Location/Qualifiers
source                  1..120
                        mol_type = protein
                        organism = Camelus bactrianus
SEQUENCE: 32
QVQLQESGGG SVQAGGSLRL SCTASGFTFD DVDMGWYRQA SGNECELVST ISSDGSTYYA   60
DSVKGRFTIS QDNAKNTVYL QMNSLKPEDT AMYYCAAARY SDYEGMCGYW SQGTQVTVSS   120

SEQ ID NO: 33           moltype = AA  length = 120
FEATURE                 Location/Qualifiers
source                  1..120
                        mol_type = protein
                        organism = Camelus bactrianus
SEQUENCE: 33
QVQLQESGGG SVQAGGSLRL SCTASGFTFD DVDMGWYRQA PGNECELVST ISSDGSTYYA   60
DSVKGRFTIS QDNAKNTVYL QMNSLKPEDT AMYYCAAARY SDYEGMCGYW SQGTQVTVSS   120

SEQ ID NO: 34           moltype = AA  length = 120
FEATURE                 Location/Qualifiers
source                  1..120
                        mol_type = protein
                        organism = Camelus bactrianus
SEQUENCE: 34
QVQLQESGGG SVQAGGSLRL SCTVSGFTFD DVDMGWYRQA PGNECELVST ISSDGSTYYA   60
DSVKGRFTIS QDNAKNTVYL QMNSLKPEDT AMYYCAAARY SDYEGMCGYW SQGTQVTVSS   120
```

```
SEQ ID NO: 35            moltype = AA   length = 120
FEATURE                  Location/Qualifiers
source                   1..120
                         mol_type = protein
                         organism = Camelus bactrianus
SEQUENCE: 35
QVQLQESGGG LVQPGGSLRL SCAASGFTFD DVDMGWYRQA PGNECELVST ISSDGSTYYA   60
DSVKGRFTIS QDNAKNTVYL QMNSLKPEDT AMYYCAAARY SDYEGMCGYW SQGTQVTVSS  120

SEQ ID NO: 36            moltype = AA   length = 120
FEATURE                  Location/Qualifiers
source                   1..120
                         mol_type = protein
                         organism = Camelus bactrianus
SEQUENCE: 36
QVQLQESGGG SVQAGESLRL SCRTSGFSFD DVDMGWYRQA PGNECELVST ISSDGSTYYA   60
DSVKGRFTIS QDNAKNTVYL QMNSLKPEDT AMYYCAAARY SDYEGMCGYW SQGTQVTVSS  120

SEQ ID NO: 37            moltype = AA   length = 120
FEATURE                  Location/Qualifiers
source                   1..120
                         mol_type = protein
                         organism = Camelus bactrianus
SEQUENCE: 37
QVQLQESGGG SVQAGETLRL SCTVSGFTFD DADMGWYRQA PGNQCELVST ISSDGITYYA   60
DSVKGRFTVS QDNAKNTVYL QMNSLKPEDT AMYYCAAARY SDYEGMCGYW SQGTQVTVSS  120

SEQ ID NO: 38            moltype = AA   length = 125
FEATURE                  Location/Qualifiers
source                   1..125
                         mol_type = protein
                         organism = Camelus bactrianus
SEQUENCE: 38
QVQLQESGGG SVQAGGSLRL SCAASGFTYT GYCMGWFRQA PGKEREGVAT VDSDGDTSYA   60
DSVKGRFTIS KDNAKNTLYL QMNSLKPEDT AMYYCAADFS RWHLCSTSLA TLGYWGQGTQ  120
VTVSS                                                              125

SEQ ID NO: 39            moltype = AA   length = 127
FEATURE                  Location/Qualifiers
source                   1..127
                         mol_type = protein
                         organism = Camelus bactrianus
SEQUENCE: 39
QVQLQESGGG SVQAGGSLRL SCAASGYTYT GYCMGWFRQA PGKEREGVAT IDSDGDTSYA   60
DSVKGRFTIS KDNAKNTLYL QMNSLKPEDT AMYYCAADFR RWHLCSSSFR EDGMDYWGKG  120
TQVTVSS                                                            127

SEQ ID NO: 40            moltype = AA   length = 127
FEATURE                  Location/Qualifiers
source                   1..127
                         mol_type = protein
                         organism = Camelus bactrianus
SEQUENCE: 40
QVQLQESGGG SVQAGETLRL SCAASGYTYT GYCMGWFRQA TGKEREGVAT IDSDGDTTYA   60
DSVKGRFTIS KDNGKNTLYL QMNSLKPEDT AMYYCAADFR RWHLCSSSFQ EYDMDYWGKG  120
TQVTVSS                                                            127

SEQ ID NO: 41            moltype = DNA   length = 369
FEATURE                  Location/Qualifiers
source                   1..369
                         mol_type = genomic DNA
                         organism = Camelus bactrianus
SEQUENCE: 41
caggtgcagc tgcaggagtc tggaggaggc tcggtgcagg ctggagagac tctgagactc   60
tcctgtacag cctctggatt cacttttgat gattctgaca tgggctggta ccgccaggct  120
ccagggaatg agtgcgagtt ggtctcaact attagtagtg atggtagcac atactatgca  180
gactccgtga agggccgatt caccatctcc aagacaacg ccaagaacac ggtgtatctg  240
caaatgaaca gcctgaaacc tgaggacaca gccgtgtatt actgtgcggc acatcccctc  300
cactacgagt tgggtacgtg cgcggcactg gactactggg gccgggggac ccaggtcacc  360
gtctcctca                                                          369

SEQ ID NO: 42            moltype = DNA   length = 369
FEATURE                  Location/Qualifiers
source                   1..369
                         mol_type = genomic DNA
                         organism = Camelus bactrianus
SEQUENCE: 42
caggtgcagc tgcaggagtc tgggggaggc tcggtgcagg ctggagagac tctgagactc   60
```

```
tcctgtacag cctctggatt cacttttgat gattctgaca tgggctggta ccgccaggct   120
ccagggaatg agtgcgagtt ggtctcaact attagtagtg atggtagcac atactatgca   180
gactccgtga agggccgatt caccatctcc aagacaacg ccaagaacgc ggtgtatctg    240
caaatgaaca gcctgaaacc tgaggacaca gccgtgtatt actgtgcggc acatcccctc   300
cactacgagt tgggtacgtg cgcggcactg gactactggg gccggggggac ccaggtcacc   360
gtctcctca                                                            369

SEQ ID NO: 43            moltype = DNA  length = 369
FEATURE                  Location/Qualifiers
source                   1..369
                         mol_type = genomic DNA
                         organism = Camelus bactrianus
SEQUENCE: 43
caggtgcagc tgcaggagtc tggaggaggc tcggtgcagg ctggagggtc tctgagactc   60
tcctgtacag cctctggatt cacttttgat gattctgatg tgcgctggta ccgccaggct   120
ccagggcgtg agtgcaagtt ggtctcaagt attagtagtg accgtagcgc atactatgaa   180
gactccgtga agggccgatt caccatctcc aagacaacg ccaagaacac ggtgtatctg    240
caaatgaaca gcctgaaacc tgaggacaca gccgtgtatt actgtgcggc acatcccctc   300
cactacgagt tgggtacgtg cgcggcactg gactactggg gccggggggac ccaggtcacc   360
gtctcctca                                                            369

SEQ ID NO: 44            moltype = DNA  length = 375
FEATURE                  Location/Qualifiers
source                   1..375
                         mol_type = genomic DNA
                         organism = Camelus bactrianus
SEQUENCE: 44
caggtgcagc tgcaggagtc tgggggaggc tcggtgcagg ctggagagac tctgagactc   60
tcctgtacag cctctggatt cacttttgat gattctgaca tgggctggta ccgccaggct   120
ccagggaatg agtgcgagtt ggtctcgcat attagtagtg atggtagcac atactatgca   180
gactccgtga agggccgatt caccatctcc aagacaacg ccaagaacac ggtctttctg    240
caaatgaaca gcctgaaacc tgaagacaca gccgtatatt actgtgcggc agataaagac   300
gcccgcggtt acgagttggg tacgtgtgag tccctggact actggggccg ggggacccag   360
gtcaccgtct cctca                                                     375

SEQ ID NO: 45            moltype = DNA  length = 354
FEATURE                  Location/Qualifiers
source                   1..354
                         mol_type = genomic DNA
                         organism = Camelus bactrianus
SEQUENCE: 45
caggtgcagc tgcaggagtc tgggggaggc tcggtgcagg ctggagggtc tctgagactc   60
tcctgtacag tctctggatt cagtttcgat gattctgaca ccgccgggct                120
ccagggaatg agtgcgagtt ggtctcaggt atcagtagag atggcagcac atactatgca   180
gactccgtga agggccgatt caccatctcc aagacaacg ccaagaactg ggtgtatctg    240
caaatgaaca gcctgaaacc tgaggacacg gccgtgtatt actgtgcggc agcgacttat   300
agcgactatg tctgtgacta ctggacacag gggacccagg tcaccgtctc ctca         354

SEQ ID NO: 46            moltype = DNA  length = 375
FEATURE                  Location/Qualifiers
source                   1..375
                         mol_type = genomic DNA
                         organism = Camelus bactrianus
SEQUENCE: 46
caggtgcagc tgcaggagtc tgggggaggc tcggtgcagg ctggagagac tctgagactc   60
tcctgtacag cctctggatt cacttttgat gattctgaca tgggctggta ccgccaggct   120
ccagggaatg agtgcgagtt ggtctcgcat attagtagtg atggtagcac atactatgca   180
gactccgtga agggccgatt caccatctcc aagacaacg ccaagaacac ggtctttctg    240
caaatgaaca gcctgaaacc tgaagacaca gccgtatatt actgtgcggc agataaagac   300
gcccgcggtt acgagttggg tacgtgtgag tccctggact actggggccg ggggacccag   360
gtcaccgtct cctca                                                     375

SEQ ID NO: 47            moltype = DNA  length = 375
FEATURE                  Location/Qualifiers
source                   1..375
                         mol_type = genomic DNA
                         organism = Camelus bactrianus
SEQUENCE: 47
caggtgcagc tgcaggagtc tgggggaggc tcggtgcagg ctggagagac tctgagactc   60
tcctgtacag cctctggatt cacttttgat gattctgaca tgggctggta ccgccaggct   120
ccagggaatg agtgcgagtt ggtctcaact attagtagtg atggtagcac atactatgca   180
gactccgtga agggccgatt caccatctcc aagacaacg ccaagaacac ggtgtatctg    240
caaatgaaca gcctgaaacc tgaggacaca gccgtgtatt actgtgcggc agataaagac   300
gcccgtggct acgagttggg tacgtgtgag tccctggact actggggccg ggggacccag   360
gtcaccgtct cctca                                                     375

SEQ ID NO: 48            moltype = DNA  length = 369
FEATURE                  Location/Qualifiers
source                   1..369
```

```
                              mol_type = genomic DNA
                              organism = Camelus bactrianus
SEQUENCE: 48
caggtgcagc tgcaggagtc tggaggaggc tcggtgcagg ctggagagac tctgagactc   60
tcctgtacag cctctggatt cacttttgat gaatctgtca tgggctggta ccgccaggct  120
ccagggaatg agtgtgagtt ggtctcaact attagtagtg atggtagcac atactattca  180
aactccgtga agggccgatt caccatctcc aagacaacg ccaagaacac ggtgtatctg  240
caaatgaaca gcctgaaacc tgaggacaca gccgtgtatt actgtgcggc cgatgatcac  300
acctacgaat tgggtacctg cgaggctctc aactactggg gccggggac ccaggtcacc  360
gtctcctca                                                         369

SEQ ID NO: 49                 moltype = DNA  length = 369
FEATURE                       Location/Qualifiers
source                        1..369
                              mol_type = genomic DNA
                              organism = Camelus bactrianus
SEQUENCE: 49
caggtgcagc tgcaggagtc tggaggaggc tcggtgcagg ctggagagac tctgagactc   60
tcctgtacag cctctggatt cacttttgat gattctgaca tgggctggta ccgccaggct  120
ccagggagtg agtgcgagtt ggtctcaact attagtagtg atggtaacac ctactattca  180
aactccgtga agggccgatt caccatctcc aagacaacg ccaagaacac ggtgtatctg  240
caaatgaaca gcctgaaacc tgaggacaca gccgtgtatt actgtgcggc agatgatcag  300
cactacgagt tgggtacctg cgaggctctc gactactggg gccggggac ccaggtcacc  360
gtctcctca                                                         369

SEQ ID NO: 50                 moltype = DNA  length = 369
FEATURE                       Location/Qualifiers
source                        1..369
                              mol_type = genomic DNA
                              organism = Camelus bactrianus
SEQUENCE: 50
caggtgcagc tgcaggagtc tggaggaggc tcggtgcagg ctggagagac tctgaaactc   60
tcctgtacag cctctggatt cacgtttgat gattctacca tggcctggta ccgccaggct  120
ccagggaatg agtgcaagtt ggtgtcaact attagtagtg atgggagcac atactatgca  180
gactccgtga agggccgatt caccatctcc aagacaacg ccaagaacac ggtgtatctg  240
caaatgaaca gcctgaaacc tgaggacaca gccgtgtatt actgtgcggc agatgatcag  300
aactacgagt taggtacctg cgaggctctc gactactggg gccggggac ccaggtcacc  360
gtctcctca                                                         369

SEQ ID NO: 51                 moltype = DNA  length = 369
FEATURE                       Location/Qualifiers
source                        1..369
                              mol_type = genomic DNA
                              organism = Camelus bactrianus
SEQUENCE: 51
caggtgcagc tgcaggagtc tgggggaggc tcggtgcagg ctggagagac tctgagactc   60
tcctgtacag cctctggatt cacttttgat gattctgaca tgggctggta ccgccaggct  120
ccagggaatg agtgcgagtt ggtctcacat attagtagtg gtggtagcac atactatgca  180
gactccgtga agggccgatt caccatctcc aagacaacg ccaagaacac ggtgtatctg  240
caaatgaaca gcctgaaacc tgaggacaca gccgtgtatt actgtgcggc agatgggagt  300
aactacgaat tgggtacgtg cgctgcctta gactactggg gccggggac ccaggtcacc  360
gtctcctca                                                         369

SEQ ID NO: 52                 moltype = DNA  length = 369
FEATURE                       Location/Qualifiers
source                        1..369
                              mol_type = genomic DNA
                              organism = Camelus bactrianus
SEQUENCE: 52
caggtgcagc tgcaggagtc tggaggaggc tcggtgcagg ctggagagac tctgagactc   60
tcctgtacag cctctggatt cacttttgat gattctgaca tgggctggta ccgccaggct  120
ccagggaatg agtgcgagtt ggtctcaact attagtagtg atggtagcac atactatgca  180
gactccgtga agggccgatt caccatctcc aagacaacg ccaagaacac ggtgtatctg  240
caaatgaaca gcctgaaacc tgaggacaca gccgtgtatt actgtgcggc agatgggcat  300
aagtacgagt tgggtacgtg cgctgcctta gactactggg gccggggac ccaggtcacc  360
gtctcctca                                                         369

SEQ ID NO: 53                 moltype = DNA  length = 369
FEATURE                       Location/Qualifiers
source                        1..369
                              mol_type = genomic DNA
                              organism = Camelus bactrianus
SEQUENCE: 53
caggtgcagc tgcaggagtc tggaggaggc tcggtgcagg ctggagagac tctgagactc   60
tcctgtacag cctctggatt cacttttgat gattctgata tgggctggta ccgccaggct  120
ccagggaatg agtgcgagtt ggtctcaact attagtgctg atggtagcac attctatgca  180
gactccgtga agggccgatt caccatctcc aagacaacg ccaagaacac ggtgtatctg  240
caaatgaaca gcctgaaacc tgaggacaca gccgtgtatt actgtgcgtc cccagagaat  300
gagtacgaat tgggtacttg cgaggcccta gattactggg gccaggggac ccaggtcacc  360
```

```
gtctcctca                                                         369

SEQ ID NO: 54           moltype = DNA   length = 372
FEATURE                 Location/Qualifiers
source                  1..372
                        mol_type = genomic DNA
                        organism = Camelus bactrianus
SEQUENCE: 54
caggtgcagc tgcaggagtc tgggggaggc tcggtgcagg ctggagagac tctgagactc  60
tcctgtacag cctctggatt cacttttgat gattctgaca tgggctggta ccgccaggct  120
ccagggaatg agtgcgagtt ggtctcaact attagtagtg atggtagcac atactatgca  180
gactccgtga agggccgatt caccatctcc aagacaacg ccaagaacac ggtgtatctg  240
caaatgaaca gcctgaaacc tgaggacaca gccgtgtatt actgtgcggc agatcatggc  300
gggggtacg agttgggtac ttgtgcggcc cttgattact ggggccgggg gacccaggtc  360
accgtctcct ca                                                     372

SEQ ID NO: 55           moltype = DNA   length = 369
FEATURE                 Location/Qualifiers
source                  1..369
                        mol_type = genomic DNA
                        organism = Camelus bactrianus
SEQUENCE: 55
caggtgcagc tgcaggagtc tgggggaggc tcggtgcagg ctggagggtc tctgagactc  60
tcctgtacag cctctagatt cacttttgat gattctgaca tgggctggta ccgccaggct  120
ccagggaatg agtgcgagtt ggtctcgact attagtagtg atggtccac atactatgca  180
aactccgtga agggccgatt caccatctcc aagacaacg ccgtatatcta  240
caaatgaaca gcctgaaacc tgaggacaca gccgtttatt actgtgcggc gttagaatgg  300
gaatacgaat tgggtacgtg cgaagccctg gattactggg gccaggggac ccaggtcacc  360
gtctcctca                                                         369

SEQ ID NO: 56           moltype = DNA   length = 369
FEATURE                 Location/Qualifiers
source                  1..369
                        mol_type = genomic DNA
                        organism = Camelus bactrianus
SEQUENCE: 56
caggtgcagc tgcaggagtc tgggggaggc tcggtgcagg ctggagggtc tctgagactc  60
tcctgtacag cctctggatt cacttttgat gattctgaca tggtctggta ccgccaggct  120
ccagggaatg agtgcgagtt ggtctcacgt attagtagtg atggtagcac atactatgca  180
gactccgtga agggccgatt caccatctcc aagacaacg ccaagaacac ggtatatcta  240
caaatgaaca gcctgaaacc tgaggacaca gccgtttatt actgtgcggc gttagaatgg  300
gaatacgaat tgggtacgtg cgaagccctg gattactggg gccaggggac ccaggtcacc  360
gtctcctca                                                         369

SEQ ID NO: 57           moltype = DNA   length = 369
FEATURE                 Location/Qualifiers
source                  1..369
                        mol_type = genomic DNA
                        organism = Camelus bactrianus
SEQUENCE: 57
caggtgcagc tgcaggagtc tgggggaggc tcggtgcagg ctggagggtc tctgagactc  60
tcctgtacag cctctggatt cacttttgat gattctgaca tgggctggta ccgccaggct  120
ccagggaatg agtgcgagtt ggtctcaact attagtagtg atggtagcac atactatgca  180
gactccgtga agggccgatt caccatctcc aagacaacg ccaagaacac ggtgtatctg  240
caaatgaaca gcctgaaacc tgaggacacg gccgtgtatt actgtgcgga cgttcagatc  300
ccctatgggt tgggtacctg tgagtcgttg gactactggg gccgggggac ccaggtcacc  360
gtctcctca                                                         369

SEQ ID NO: 58           moltype = DNA   length = 366
FEATURE                 Location/Qualifiers
source                  1..366
                        mol_type = genomic DNA
                        organism = Camelus bactrianus
SEQUENCE: 58
caggtgcagc tgcaggagtc tgggggaggc tcggtgcagg ctggacagac tctgagactc  60
tcctgtacag cctctggatt cacttttgat gattctgaca tggcctggta ccgccaggct  120
ccagggaatg agtgcgagtt ggtctcaaaa atgcgtagtg atggtagcac atactatgca  180
gactccgtga agggccgctt caccatctcc aagacaacg cgaagaacac ggtgtatctg  240
caaatgaaca gcctgaaacc tgaggacaca gccgtgtatt actgtgcgga gggatttgccc  300
tacggggttgg gtacttgcac ttccctggac tactggggcc ggggacccca ggtcaccgtc  360
tcctca                                                            366

SEQ ID NO: 59           moltype = DNA   length = 375
FEATURE                 Location/Qualifiers
source                  1..375
                        mol_type = genomic DNA
                        organism = Camelus bactrianus
SEQUENCE: 59
caggtgcagc tgcaggagtc tgggggaggc tcggtgcagg ctggagggtc tctgagactc  60
```

```
tcctgtacag cctccggatt cacttttgat gattctgatt ctgacatggg ctggtaccgc    120
caggctccag ggaacgagtg cgagttggtc tcatctatta gtagtgatgg tagcacatac   180
tatgcagact ccgtgaaggg ccgattcacc atctcccaag acaacgccaa gaacacggtg   240
tatctgcaaa tgaacagcct gaaacctgag gacacagccg tgtattactg tgcagccatt   300
aattctgggt acgagttggg tacttgcgag tcgttggact actggggccg ggggacccag   360
gtcaccgtct cctca                                                    375

SEQ ID NO: 60           moltype = DNA   length = 369
FEATURE                 Location/Qualifiers
source                  1..369
                        mol_type = genomic DNA
                        organism = Camelus bactrianus
SEQUENCE: 60
caggtgcagc tgcaggagtc tgggggaggc tcggtgcagg ctggagggtc tctgcgactc    60
tcctgtacag cctctggatt cacttttgat gattctgtga tgggctggtt ccggaaggct   120
ccagggaatg agtgcgagtt ggtctcaact attagtagtg atggtagcac atactatgca   180
gactccgtga agggccgatt caccatctcc aagacaacg ccaagaacac ggtgtatctg   240
caaatgaaca acctgaaacc tgaggacacg gccgtgtatt actgtgcagc cattaattct   300
gggtacgagt tgggtacttg cgagtcgttg gactactggg gccgggggac ccaggtcacc   360
gtctcctca                                                           369

SEQ ID NO: 61           moltype = DNA   length = 375
FEATURE                 Location/Qualifiers
source                  1..375
                        mol_type = genomic DNA
                        organism = Camelus bactrianus
SEQUENCE: 61
caggtgcagc tgcaggagtc tggaggaggc ttggtccagc ctaggggggtc tctgagactc    60
tcctgtacag cctctggatt cacttttgat gattctgatt ctgacatggg ctggtaccgc   120
caggctccag ggaacgagtg cgagttggtc tcatctatta gtagtgatgg tagcacatac   180
tatgcagact ccgtgaaggg ccgattcacc atctcccaag acaacgccaa gaacacggtg   240
tatctgcaaa tgaacagcct gaaacctgag gacacagccg tgtattactg tgcagccatt   300
aattctgggt acgagttggg tacttgcgag tcgttggact actggggccg ggggacccag   360
gtcaccgtct cctca                                                    375

SEQ ID NO: 62           moltype = DNA   length = 369
FEATURE                 Location/Qualifiers
source                  1..369
                        mol_type = genomic DNA
                        organism = Camelus bactrianus
SEQUENCE: 62
caggtgcagc tgcaggagtc tgggggaggc tcggtgcagg ctggagggtc tctgagactc    60
tcctgtacag cctctggatt cacttttgat gattctgaca tgggctggta ccgccaggct   120
ccagggaatg agtgcgagtt ggtctcacgt attagtcgtg atggtaccac atactatgca   180
gactccgtga agggccgatt caccatctcc aagacaacg ccaagaacac ggtgtatctg   240
caaatgaaca gcctgaaacc tgaggacaca gccgtgtatt actgtgcgga cattaattct   300
gggtacgagt tgggtacttg cgagtcgttg gactactggg gccgggggac ccaggtcacc   360
gtctcctca                                                           369

SEQ ID NO: 63           moltype = DNA   length = 369
FEATURE                 Location/Qualifiers
source                  1..369
                        mol_type = genomic DNA
                        organism = Camelus bactrianus
SEQUENCE: 63
caggtgcagc tgcaggagtc tgggggaggc tcggtgcagg ctggagggtc tctgaaactc    60
tcctgttcag cctctggatt cacttttgat gatactgaca tgggctggta ccgccaggct   120
ccagggaatg agtgcgagtt ggtctcaact attagtagtg atggtaccac atactataca   180
gactccgtga agggccgatt caccatctcc aagacaacg ccaagaacac ggtgtatctg   240
caaatgaaca gcctgaaacc tgaggacaca gccgtgtatt actgtgcagc cattaattct   300
gggtacgagt tgggtacttg cgagtcgttg gactactggg gccgggggac ccaggtcacc   360
gtctcctca                                                           369

SEQ ID NO: 64           moltype = DNA   length = 375
FEATURE                 Location/Qualifiers
source                  1..375
                        mol_type = genomic DNA
                        organism = Camelus bactrianus
SEQUENCE: 64
caggtgcagc tgcaggagtc tggaggaggc tcggtgcagg ctggagagac tctgagactc    60
tcctgtacag cctccggatt cacttttgat gattctgatt ctgacatggg ctggtaccgc   120
caggctccag ggaacgagtg cgagttggtc tcatctatta gtagtgatgg tagcacatac   180
tatgcagact ccgtgaaggg ccgattcacc atctcccaag acaacgccaa gaacacggtg   240
tatctgcaaa tgaacagcct gaaacctgag gacacagccg tgtattactg tgcagccatt   300
aattctgggt acgagttggg tacttgcgag tcgttggact actggggccg ggggacccag   360
gtcaccgtct cctca                                                    375

SEQ ID NO: 65           moltype = DNA   length = 375
FEATURE                 Location/Qualifiers
```

```
source                      1..375
                            mol_type = genomic DNA
                            organism = Camelus bactrianus
SEQUENCE: 65
caggtgcagc tgcaggagtc tgggggaggc tcggtgcagg ctggagagac tctgagactc    60
tcctgtacag cctccggatt cacttttgat gattctgatt ctgacatggg ctggtaccgc   120
caggctccag ggaacgagtg cgagtttggt tcatctatta gtagtgatgg tagcacatac   180
tatgcagact ccgtgaaggg ccgattcacc atctcccaag acaacgccaa gaacacggtg   240
tatctgcaaa tgaacagccc gaaacctgag gacacagccg tgtattactg tgcagccatt   300
aattctgggt acgagttggg tacttgcgag tcgttggact actggggccg ggggacccag   360
gtcaccgtct cctca                                                    375

SEQ ID NO: 66               moltype = DNA   length = 369
FEATURE                     Location/Qualifiers
source                      1..369
                            mol_type = genomic DNA
                            organism = Camelus bactrianus
SEQUENCE: 66
caggtgcagc tgcaggagtc tggaggaggc tcggtgcagg ctggagagac tctgagactc    60
tcctgtacag cctctggatt cacttttgat gattctgaca tgggctggta ccgccaggct   120
ccagggaatg agtgcgagtt ggtctcaagt atcagtagtg atggtagcac atactatgca   180
gactccgtga agggccgatt caccatctcc aagacaacg caagaacac ggtgtatctg   240
caaatgaaca gcctgaaacc tgaggacaca gccgtgtatt actgtgcggc agaggggcac   300
cgttacgagt tgggtacgtg tgcagcgtta gactactggg gccgggggac ccaggtcacc   360
gtctcctca                                                           369

SEQ ID NO: 67               moltype = DNA   length = 369
FEATURE                     Location/Qualifiers
source                      1..369
                            mol_type = genomic DNA
                            organism = Camelus bactrianus
SEQUENCE: 67
caggtgcagc tgcaggagtc tggaggaggc tcggtgcagg ctggagagac tctgagactc    60
tcctgtacag cctctggatt cacttttgat gattctgaca tgggctggta ccgccaggct   120
ccagggaatg agtgcgagtt ggtctcaact attagtagtg atggtagcac atactatgca   180
gactccgtga agggccgatt caccatctcc aagacaacg ccaagaacac ggtgtatctg   240
caaatgaaca gcctgaaacc tgaggacaca gccgtgtatt actgtgcggc agatgggcat   300
aagtacgagt gggtacgtg cgctgcctta gactactggg gccgggggac ccaggtcacc   360
gtctcctca                                                           369

SEQ ID NO: 68               moltype = DNA   length = 369
FEATURE                     Location/Qualifiers
source                      1..369
                            mol_type = genomic DNA
                            organism = Camelus bactrianus
SEQUENCE: 68
caggtgcagc tgcaggagtc tggaggaggc ttggtgcagc ctgggggtc tctgagactc    60
tcctgtgcag cctctggatt cacttttggt gattctggca tgggctggta ccgccaggct   120
ccagggaatg agtgcgagtt ggtctcaagt gtgagtagtg atggtagcac atactatgca   180
gactccgtga agggccgatt caccatctcc aagacaacg ccaagaacac ggtgtatctg   240
cgaatgaaca gcctgaaacc tgaggacaca gccgtgtatt actgtgcggc agatgatcac   300
aagtacgaat tgggtacctg cgaggctctc gactactggg gccgggggac ccaggtcacc   360
gtctcctca                                                           369

SEQ ID NO: 69               moltype = DNA   length = 369
FEATURE                     Location/Qualifiers
source                      1..369
                            mol_type = genomic DNA
                            organism = Camelus bactrianus
SEQUENCE: 69
caggtgcagc tgcaggagtc tggaggaggc tcggtgcagg ctggagggtc tctgagactc    60
tcctgtacag cctctggatt cacttttgat gatcttgaca tgcgctggta ccgccaggct   120
ccagggaatg agtgcgagtt ggtctcaatt attaatagtg atggtagaac atactatgca   180
gactccgtga agggccgatt cgccatctcc cagaacaacg ccaaaaacac ggtgtatctg   240
caaatgaaca gcctgaaacc tgaggacaca gccgtgtatt actgtgcggc agatcaacac   300
cgctacggat tgggtacgtg cgaggcctta gactactggg gccgggggac ccaggtcacc   360
gtctcctca                                                           369

SEQ ID NO: 70               moltype = DNA   length = 369
FEATURE                     Location/Qualifiers
source                      1..369
                            mol_type = genomic DNA
                            organism = Camelus bactrianus
SEQUENCE: 70
caggtgcagc tgcaggagtc tgggggaggc tcggtgcagg ctggagagac tctgagactc    60
tcctgtacag cctctggatt cacttttgat gattctgaca tgggctggta ccgccaggct   120
ccagggaatg agtgcgagtt ggtctctact attagtagtg atggtagaac atactatgca   180
gactccgtga agggccgatt cgccatctcc cagaacaacg ccaaaaacac ggtgtatctg   240
caaatgaaca gcctgaaacc tgaggacaca gccgtgtatt actgtgcggc agatcaacac   300
```

```
cgctacggat tgggtacgtg cgaggcctta gactactggg gccggggggac ccaggtcacc    360
gtctcctca                                                              369
```

SEQ ID NO: 71          moltype = DNA   length = 366
FEATURE                Location/Qualifiers
source                 1..366
                       mol_type = genomic DNA
                       organism = Camelus bactrianus
SEQUENCE: 71
```
caggtgcagc tgcaggagtc tggaggaggc tcggtgcagg ctggagagac tctgagactc    60
tcctgtacag cctctggatt cacttttaat gattctaaca tggggtggta ccgccaggct   120
ccagggcatg agtgcgaatt ggtctcaact attagtagcg atggtagcac atactatgca   180
gactccgtga agggccgatt caccatctcc caaaacaacg ccaggaacac cgtgtatctg   240
caaatgaaca gcctgaaacc tgaggacaca gccgtgtatt actgtgcggg agactggggc   300
tacgagttgg gtatttgcac ctcactagac tactgggggcc aggggaccca ggtcaccgtc   360
tcctca                                                              366
```

SEQ ID NO: 72          moltype = DNA   length = 360
FEATURE                Location/Qualifiers
source                 1..360
                       mol_type = genomic DNA
                       organism = Camelus bactrianus
SEQUENCE: 72
```
caggtgcagc tgcaggagtc tggaggaggc tcggtgcagg ctggagggtc tctgagactc    60
tcctgtacag cctctggatt cacttttgat gatgttgaca tgggctggta ccgccaggct   120
tcagggaatg agtgcgagtt ggtctcgact attagtagtg atggtagtac atactatgca   180
gactccgtga agggccgatt caccatctcc caagacaacg ccaagaacac ggtatatctg   240
caaatgaaca gcctgaaacc tgaggacacg gccatgtatt actgtgcggc agcccgctat   300
agcgactatg aagggatgtg cggttactgg agccagggga cccaggtcac cgtctcctca   360
```

SEQ ID NO: 73          moltype = DNA   length = 360
FEATURE                Location/Qualifiers
source                 1..360
                       mol_type = genomic DNA
                       organism = Camelus bactrianus
SEQUENCE: 73
```
caggtgcagc tgcaggagtc tggaggaggc tcggtgcagg ctggagggtc tctgagactc    60
tcctgtacag cctctggatt cacttttgat gatgttgaca tgggctggta ccgccaggct   120
ccagggaatg agtgcgagtt ggtctcaact attagtagtg atggtagtac atactatgca   180
gactccgtga agggccgatt caccatctcc caagacaacg ccaagaacac ggtatatctg   240
caaatgaaca gcctgaaacc tgaggacacg gccatgtatt actgtgcggc agcccgctat   300
agcgactatg aagggatgtg cggttactgg agccagggga cccaggtcac cgtctcctca   360
```

SEQ ID NO: 74          moltype = DNA   length = 360
FEATURE                Location/Qualifiers
source                 1..360
                       mol_type = genomic DNA
                       organism = Camelus bactrianus
SEQUENCE: 74
```
caggtgcagc tgcaggagtc tgggggaggc tcggtgcagg ctggagggtc tctgagactc    60
tcctgtacag tctctggatt cacttttgat gatgttgaca tgggctggta ccgccaggct   120
ccagggaatg agtgcgagtt ggtctcaact attagtagtg atggtagtac atactatgca   180
gactccgtga agggccgatt caccatctcc caagacaacg ccaagaacac ggtatatctg   240
caaatgaaca gcctgaaacc tgaggacacg gccatgtatt actgtgcggc agcccgctat   300
agcgactatg aagggatgtg cggttactgg agccagggga cccaggtcac cgtctcctca   360
```

SEQ ID NO: 75          moltype = DNA   length = 360
FEATURE                Location/Qualifiers
source                 1..360
                       mol_type = genomic DNA
                       organism = Camelus bactrianus
SEQUENCE: 75
```
caggtgcagc tgcaggagtc tggaggaggc ttggtgcagc ctgggggggtc tctgagactc    60
tcctgtgcag cctctggatt cacttttgat gatgttgaca tgggctggta ccgccaggct   120
ccagggaatg agtgcgagtt ggtctcaact attagtagtg atggtagtac atactatgca   180
gactccgtga agggccgatt caccatctcc caagacaacg ccaagaacac ggtatatctg   240
caaatgaaca gcctgaaacc tgaggacacg gccatgtatt actgtgcggc agcccgctat   300
agcgactatg aagggatgtg cggttactgg agccagggga cccaggtcac cgtctcctca   360
```

SEQ ID NO: 76          moltype = DNA   length = 360
FEATURE                Location/Qualifiers
source                 1..360
                       mol_type = genomic DNA
                       organism = Camelus bactrianus
SEQUENCE: 76
```
caggtgcagc tgcaggagtc tggaggaggc tcggtgcagg ctggagagag tctgagactc    60
tcctgtagaa cctctggatt cagttttgat gatgttgaca tgggctggta ccgccaggct   120
ccagggaatg agtgcgagtt ggtctcaact attagtagtg atggtagtac atactatgca   180
gactccgtga agggccgatt caccatctcc caagacaacg ccaagaacac ggtatatctg   240
```

-continued

```
caaatgaaca gcctgaaacc tgaggacacg gccatgtatt actgtgcggc agcccgctat    300
agcgactatg aagggatgtg cggttactgg agccagggga cccaggtcac cgtctcctca    360

SEQ ID NO: 77          moltype = DNA  length = 360
FEATURE                Location/Qualifiers
source                 1..360
                       mol_type = genomic DNA
                       organism = Camelus bactrianus
SEQUENCE: 77
caggtgcagc tgcaggagtc tggaggaggc tcggtgcagg ctggagagac tctgagactc    60
tcctgtacag tctctggatt cactttgat gatgctgaca tgggctggta ccgccaggct    120
ccagggaatc agtgcgagtt ggtctcaact attagtagtg atggtatcac atactatgca    180
gactccgtga agggccgatt caccgtctcc aagacaacg ccaagaacac ggtatatctg    240
caaatgaaca gcctgaaacc tgaggacacg gccatgtatt actgtgcggc agcccgctat    300
agcgactatg aagggatgtg cggttactgg agccagggga cccaggtcac cgtctcctca    360

SEQ ID NO: 78          moltype = DNA  length = 375
FEATURE                Location/Qualifiers
source                 1..375
                       mol_type = genomic DNA
                       organism = Camelus bactrianus
SEQUENCE: 78
caggtgcagc tgcaggagtc tggaggaggc tcggtgcagg ctggagggtc tctgagactc    60
tcctgtgcag cctctggatt tacctacact ggctactgca tgggctggtt ccgccaggct    120
ccagggaagg agcgcgaggg ggtcgcaacg gttgatagtg atggtgacac aagctacgca    180
gactccgtga agggccgatt caccatctcc aaagacaacg ccaagaacac tctgtatctg    240
caaatgaaca gcctgaaacc tgaggacact gccatgtact actgtgcggc agatttttcg    300
cggtggcacc tatgttcaac aagcctagct accttgggtt actggggcca ggggacccag    360
gtcaccgtct cctca                                                     375

SEQ ID NO: 79          moltype = DNA  length = 381
FEATURE                Location/Qualifiers
source                 1..381
                       mol_type = genomic DNA
                       organism = Camelus bactrianus
SEQUENCE: 79
caggtgcagc tgcaggagtc tggaggaggc tcggtgcagg ctggaggatc tctgagactc    60
tcctgtgcag cctctggata cacctacact ggctactgca tgggctggtt ccgccaggct    120
ccagggaagg agcgcgaggg ggtcgcaact attgatagtg atggtgacac aagctacgca    180
gactccgtga agggccgatt caccatctcc aaagacaacg ccaagaacac tctgtatctg    240
caaatgaaca gcctgaaacc tgaggacact gccatgtact actgtgcggc agactttcgc    300
cgctggcacc tatgtagtag ttcgtttcgg gaagacggca tggactactg ggcaaagga    360
acccaggtca ccgtctcctc a                                              381

SEQ ID NO: 80          moltype = DNA  length = 381
FEATURE                Location/Qualifiers
source                 1..381
                       mol_type = genomic DNA
                       organism = Camelus bactrianus
SEQUENCE: 80
caggtgcagc tgcaggagtc tgggggaggc tcggtgcagg ctggagagac tctgagactc    60
tcctgtgcag cctctggata cacctacact ggctactgca tgggctggtt ccgccaggct    120
acagggaagg agcgcgaggg ggtcgcaact attgatagtg atggagacac aacctacgca    180
gactccgtga agggccgatt caccatctcc aaagacaacg gcaagaacac tctgtatctg    240
caaatgaaca gcctgaaacc tgaggacact gccatgtact actgtgcggc agactttcgc    300
cgctggcacc tatgtagtag ctcgtttcag gagtacgaca tggactactg ggcaaagga    360
acccaggtca ccgtctcctc a                                              381
```

ANTI-HER2 NANOBODY AND CODING SEQUENCE AND USE THEREOF

CROSS-REFERENCE TO RELATED APPLICATIONS

This application is a continuation of U.S. application Ser. No. 16/624,403, filed Dec. 19, 2019, which is a 35 U.S.C. § 371 national stage filing of International Application No. PCT/CN2018/091953, filed on Jun. 20, 2018, which claims priority to Chinese Patent Application No. 201710471319.6, filed on Jun. 20, 2017. The entire contents of each of the aforementioned applications are expressly incorporated herein by reference.

SEQUENCE LISTING

The instant application contains a Sequence Listing XML which has been submitted electronically in XML format and is hereby incorporated by reference in its entirety. Said XML copy, created on Oct. 17, 2022, is named 130535-00203.xml and is 89,303 bytes in size.

TECHNICAL FIELD

The invention relates to the field of biomedical or biopharmaceutical technology, and particularly to anti-Her2 nanobody and its coding sequence and application.

TECHNICAL BACKGROUND

Human epidermal growth factor receptor-2 (Her2/ErbB2), also known as Her2/Neu, ErbB-2, CD340 or p185, is a protein encoded by human Her2 gene. Her2 is a receptor tyrosine kinase (RTK) belonging to the epidermal growth factor receptor (EGFR/ErbB) family. It consists of 1255 amino acids, including four extracellular domains (I, II, III and IV) and one transmembrane domain. It also has a tyrosine kinase activity domain and a carboxyl terminal tail containing tyrosine residues with intracellular signal molecular anchor site. The molecular weight of HER2 is about 185kD. Members of the EGFR family have similar structures. Their extracellular domain I and III are involved in the binding of receptors to ligands while extracellular domain II and IV are involved in receptor dimerization. The binding of receptors to ligands results in receptor conformational changes and receptor activation. Her2 has a special open structure, which can activate itself without the involvement of specific ligands. Her2 forms homodimer or heterodimer with other receptors of the EGFR family and is the preferred molecule for heterodimerization among family members.

Her2 is overexpressed in breast cancer, ovarian cancer, prostate cancer, gastric cancer, lung cancer and other epitherlial cell-derived malignant tumors while low-expressed or unexpressed in normal tissues. When the expression level of Her2 is low, the receptor proteins generally exist in monomers with low tyrosine kinase activity. Overexpression of Her2 may lead to persistent and enhanced activation of receptor tyrosine kinase. A series of downstream reaction cascade, including mitogen-activated protein kinase (MAPK), phosphatidylinositol-3-kinase-protein kinase B/Akt (PI3K-PKB/Akt), phospholipase C-protein kinase C (PLC-PKC), transcription signal transduction and activation protein (STAT) and other major signaling pathways, may also be triggered. Her2-mediated signaling pathway can also regulate the expression of tumor-related genes, such as upregulating the expression of vascular endothelial growth factor (VEGF), urokinase type plasmin activator (UPA), cyclooxygenase-2 (Cox-2) and chemokine receptor CXCR-4 or downregulating the expression of MMP inhibitor RECK, and promote tumor invasion and metastasis. Amplification or overexpression of Her2 plays an important role in tumorigenesis and growth of certain invasive breast cancer. Therefore, Her2 has become an important biomarker and therapeutic target for breast cancer.

Humanized recombinant monoclonal antibodies, Trastuzumab and Pertuzumab, are conventional targeted therapies in breast cancer patients with Her2/neu overexpression or gene amplification. Trastuzumab endocytosis into the tumor nucleus by binding to the near-membrane region of extracellular of Her2. The binding of Trastuzumab blocks the recirculation of Her2 to the cell membrane and accelerates the bypass degradation of Her2 protein, thus inhibiting the transduction of Her2 to malignant phenotype of tumor cells. Trastuzumab is effective for patients with primary invasive breast cancer with overexpression of Her2. Antigen binding site of Pertuzumab is located at extracellular domain II of Her2, where ligand binding blocks cell signal transmission by interfering the formation of dimers between Her2 and other ErbB members. Pertuzumab has anti-tumor effect regardless of Her2 expression.

Conventional monoclonal antibodies have complex production process and high production cost. Moreover, the size of conventional monoclonal antibodies makes it difficult to penetrate tissue, resulting in low effective concentration in the tumor area and insufficient therapeutic effect. Conventional monoclonal antibodies has high immunogenicity and is always difficult to achieve the original affinity after modification. The long-term development of fully humanized traditional antibodies, high production costs, insufficient stability and many other factors limit its application and popularity in the clinic. Nanobodies are currently the smallest antibody binding domain with molecular weight of 1/10 of that of a conventional antibody. In addition to the antigenic reactivity of monoclonal antibodies, nanobodies also have some unique functional characteristics, such as low molecular weight, strong stability, good solubility, easy expression, weak immunogenicity, strong penetration, strong targeting, simple humanization, low production cost etc. Nanobodies overcome shortcomings of conventional antibodies, such as long development cycle, low stability and harsh preservation conditions. Unique structure of nanobodies also makes them suitable for carrying radioisotope. Nanobodies can penetrate the tumor tissue binding target quickly and specifically, while the non-binding nanobodies can be quickly removed from the blood and reduce the radiation dose of the body. Compared to conventional antibodies, nanobodies have more advantages as tracers and targeted internal radiotherapy drugs.

Currently, there is a lack of satisfactory nanobody against Her2 in the field. Therefore, there is an urgent need to develop new and effective specific nanobody against Her2.

SUMMARY OF THE INVENTION

The object of the present invention is to provide a class of specific nanobodies that are effective in targeting against Her2.

In first aspect of the present invention, a VHH chain of an anti-Her2 nanobody is provided. Amino acid sequence of the VHH chain is shown as any one of SEQ ID NOs.: 1-40.

In another preferred embodiment, amino acid sequence of the VHH chain is shown as any one of SEQ ID NOs.: 8, 7, 15, 12, 27, 11, 32, 13, 14, 9, 21, 30, 17, 24, 16, 6, 28, 25, 10, and 1.

In another preferred embodiment, amino acid sequence of the VHH chain is shown as any one of SEQ ID NOs.: 8, 7, 15, 12, 27, 11, 32, and 13.

In another preferred embodiment, amino acid sequence of the VHH chain is shown as any one of SEQ ID NOs.: 9, 10, 13, 17, 22, 23, and 26.

In another preferred embodiment, the HER2 is human Her2.

Furthermore, a VHH chain of anti-Her2 nanobody is provided, the VHH comprises a frame region (FR) and a complementary determination region (CDR), where the CDR includes the corresponding CDR1, CDR2 and CDR3 of any one of SEQ ID NOs.: 1-40, as well as FR1, FR2, FR3, FR4 separated by the CDR 1-3.

Furthermore, a heavy chain variable region of an anti-human Her2 antibody is provided, the heavy chain variable region comprises three complementary determining regions, CDR1, CDR2, and CDR3, and the three CDRs comprise the corresponding CDR1, CDR2 and CDR3 of any one of SEQ ID NOs.:1-40.

Furthermore, a complementary determinant region CDR region of an anti-human Her2 antibody is provided. The complementary determining region CDR region includes CDR1, CDR2 and CDR3 shown in the underlined amino acid sequence of SEQ ID NOs.:1-40 (The three underlined parts of each VHH amino acid sequence represent CDR1, CDR2 and CDR3 in turn).

In the second aspect of the present invention, an anti-Her2 nanobody is provided, which is a nanobody against Her2 epitope, and has a VHH chain as shown in the amino acid sequence of any one of SEQ ID NOs.: 1-40.

In another preferred embodiment, the preferred anti-Her2 nanobody has an amino acid sequence of the preferred VHH chain in the first aspect.

In the third aspect of the invention, a polynucleotide is provided and the polynucleotide encodes a protein selected from the group consisting of the VHH chain of the anti-Her2 nanobody in the first aspect, or the anti-Her2 nanobody in the second aspect.

In another preferred embodiment, the polynucleotide comprises DNA or RNA.

In another preferred embodiment, the polynucleotide has a nucleotide sequence as shown in any one of SEQ ID NOs.: 41-80.

In the fourth aspect of the invention, an expression vector containing the polynucleotide in the third aspect is provided.

In another preferred embodiment, the expression vector is selected from the group consisting of: DNA, RNA, virus vector, plasmid, transposon, other gene transfer system, or combination of them. Preferred expression vector includes virus vector, such as lentivirus, adenovirus, AAV virus, a retrovirus, and a combination thereof.

In the fifth aspect of the invention, a host cell is provided. The host cell contains the expression vector of the fourth aspect, or the polynucleotide of the third aspect is integrated within the genome of the host cell.

In another preferred embodiment, the host cell includes a eukaryote or prokaryote.

In another preferred embodiment, the host cell is selected from the group consisting of *Escherichia coli* and yeast cell.

In the sixth aspect of the invention, a method for producing an anti-Her2 nanobody is provided, comprising the steps of:

(a) culturing the host cells described in the fifth aspect of the invention under suitable condition for producing a nanobody, thereby obtaining a culture containing the anti-Her2 nanobody; and (b) isolating or recovering the anti-Her2 nanobody from the culture.

In another preferred embodiment, the anti-Her2 nanobody has an amino acid sequence as shown in any of SEQ ID NOs.:1-40.

In the seventh aspect of the invention, an immunoconjugate is provided, and the immunoconjugate comprises:

(a) the VHH chain of the anti-Her2 nanobody as described in the first aspect of the invention, or the anti-Her2 nanobody as described in the second aspect of the invention; and (b) a conjugating part selected from the group consisting of a detectable marker, drug, toxin, cytokine, radionuclide, or enzyme, gold nanoparticle/nanorod, magnetic nanoparticle, viral coat protein or VLP, and a combination thereof.

In another preferred embodiment, the radionuclide includes:

(i) a diagnostics radioisotope selected from the group consisting of Tc-99m, Ga-68, F-18, I-123, I-125, I-131, In-111, Ga-67, Cu-64, Zr-89, C-11, Lu-177, Re-188, and a combination thereof; and/or (ii) a therapeutic radioisotope selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133 Yb-169, Yb-177, and a combination thereof.

In another preferred embodiment, the conjugating part is a drug or toxin.

In another preferred embodiment, the drug is a cytotoxic drug.

In another preferred embodiment, the cytotoxic drug is selected from the group consisting of an antitubulin drug, DNA sulcus binding reagent, DNA replication inhibitor, alkylation reagent, antibiotic, folic acid antagonist, antimetabolic drug, chemosensitizer, topoisomerase inhibitor, *Catharanthus roseus* alkaloid and a combination thereof.

Example of particularly useful cytotoxic drug includes: DNA sulcus binding reagent, DNA alkylation reagent, and tubulin inhibitor, and typical cytotoxic drug such as auristatins, camptothecins, doxycycline/duocarmycins, etoposides, maytansines and maytansinoids (compounds such as DM1 and DM4), taxanes, benzodiazepines, or benzodiazepine containing drugs (such as pyrrolo [1,4] benzodiazepine (PBDs), indolinobenzodiazepines, and oxazolidinobenzodiazepines), vinca alkaloids, and a combination thereof.

In another preferred embodiment, the toxin is selected from the group consisting of:

Auristatins (for example, Auristatin A, Auristatin F, MMAE and MMAF), chlortetracycline, metotanol, ricin, ricin A chain, cobustatin, docamicin, Dora statin, adriamycin, daunorubicin, paclitaxel, cisplatin, cc1065, ethidium bromide, mitomycin, etoposide, tenoposide, vincristine, vinblastine, colchicine, dihydroxyanthracnose diketone, actinomycin, diphtheria toxin, *Pseudomonas* exotoxin (PE) A, PE40, abrin, abrin A chain, modeccin A chain, α-Sarcina, gelonin, mitogellin, retstrictocin, phenomycin, enomycin, curicin, crotin, calicheamicins, *Sapaonaria officinalis* inhibitor, glucocorticoid and a combination thereof.

In another preferred embodiment, the conjugating part is a detectable marker.

In another preferred embodiment, the conjugate is selected from the group consisting of fluorescent or luminous markers, radioactive markers, magnetic resonance imaging (MRI) or computerized X-ray tomography (CT) contrast agents; or enzymes, radionuclides, biotoxins, cytokines (such as IL-2, etc.), antibodies, antibody Fc fragments, antibody scFv fragments, gold nanoparticles/nanorods, viral particles, liposomes, magnetic nanoparticles, prodrug activating enzymes (e.g., DT-diaphorase (DTD) or biphenyl hydrolase-like protein (BPHL), chemotherapy agents (for example, cisplatin) or any form of nanoparticles, etc. that capable of producing detectable products.

In another preferred embodiment, the immunoconjugate contains multivalent (such as bivalent) VHH chain of the anti-Her2 nanobody as described in the first aspect of invention and the anti-Her2 nanobody as described in the second aspect of invention.

In another preferred embodiment, the multivalent refers that the amino acid sequence of the immunoconjugate includes a plurality of repetitive VHH chains of the anti-Her2 nanobody as described in the first aspect of invention and the anti-Her2 nanobody in the second aspect of invention.

In another preferred embodiment, the immunoconjugate is used for the diagnosis or prognosis of cancer, specifically for tumors expressing Her2 (i.e. Her2 positive tumors).

In another preferred embodiment, the detection is in vivo or in vitro.

In another preferred embodiment, the immunoconjugate is used for the diagnosis and/or treatment of tumors expressing Her2 protein.

In the eighth aspect of the invention, a use of the anti-Her2 nanobody described in the second aspect of invention or the immunoconjugate in the seventh aspect of invention is provided, for preparing (a) a reagent for detecting Her2 molecules; or (b) a medicament for treating tumors.

In another preferred embodiment, the conjugating part of the immunoconjugate is a diagnostic isotope.

In another preferred embodiment, the reagent is one or more reagents selected from the group consisting of isotope tracer, contrast agent, flow detection reagent, cellular immunofluorescence detection reagent, magnetic nanoparticles and imaging agent.

In another preferred embodiment, the reagent for detecting Her2 molecule is a contrast agent for (in vivo) detecting Her2 molecule.

In another preferred embodiment, the detection is in vivo or in vitro.

In another preferred embodiment, the detection includes flow detection, or cellular immunofluorescence detection.

In the ninth aspect of the invention, a pharmaceutical composition is provided, comprising:
  (i) the VHH chain of the anti-Her2 nanobody described in the first aspect of invention, or the anti-Her2 nanobody as described in the second aspect of invention, or the immunoconjugate described in the seventh aspect of invention; and
  (ii) a pharmaceutically acceptable carrier.

In another preferred embodiment, the conjugating part of the immunoconjugate is a drug, toxin, and/or therapeutic isotope.

In another preferred embodiment, the pharmaceutical composition further comprises other drugs for treating tumors, such as cytotoxic drugs.

In another preferred embodiment, the pharmaceutical composition is used for the treatment of tumors expressing Her2 protein (i.e. Her2 positive).

In another preferred embodiment, the pharmaceutical composition is in a form of injection.

In another preferred embodiment, the pharmaceutical composition is used for preparing a drug for treating the tumor selected from the group consisting of gastric cancer, liver cancer, leukemia, renal tumor, lung cancer, small intestinal cancer, bone cancer, prostate cancer, colorectal cancer, breast cancer, colon cancer, prostate cancer, cervical cancer, lymphoma, adrenal tumor, or bladder tumor.

The tenth aspect of the invention provides one or more use of the anti-Her2 nanobody described in the second aspect of invention, or the immunoconjugate described in seventh aspect of the invention:
  (i) for detecting human Her2 molecule;
  (ii) for flow cytometry assay;
  (iii) for cellular immunofluorescence detection;
  (iv) for treating tumors;
  (v) for tumor diagnosis.

In another preferred embodiment, the tumor is a tumor expressing Her2 protein (i.e. Her2 positive).

In another preferred embodiment, the use is non-diagnostic and non-therapeutic.

The eleventh aspect of the invention further provides an antibody having the heavy chain variable region VHH as described in the first aspect of the invention.

In another preferred embodiment, the antibody is a specific antibody against Her2 protein.

In another preferred embodiment, the antibody is a nanobody.

The twelfth aspect of the invention provides a recombinant protein having:
  (i) the sequence of heavy chain variable region VHH as described in the first aspect of invention or the sequence of nanobody as described in the second aspect of invention; and
  (ii) an optional tag sequence assisting expression and/or purification.

In another preferred embodiment, the tag sequence includes 6 His tag and HA tag.

In another preferred embodiment, the recombinant protein specifically binds to the Her2 protein.

The thirteenth aspect of the invention provides a use of the VHH chain as described in the first aspect of invention, the nanobody as described in the second aspect of invention, or the immunoconjugate described in the seventh aspect of invention, for preparing a medicament, agent, detecting plate or kit;
  wherein the reagent, detecting plate or kit is used for detecting Her2 protein in the sample;
  wherein the medicant is used for treating or preventing a tumor expressing Her2 protein (i.e. Her2 positive).

In another preferred embodiment, the tumor includes melanoma, gastric cancer, lymphoma, liver cancer, leukemia, renal tumor, lung cancer, small intestinal cancer, bone cancer, prostate cancer, colorectal cancer, breast cancer, colon cancer, prostate cancer and adrenal tumor.

In the fourteenth aspect of the invention, a method for detecting Her2 protein in a sample is provided. The method comprises the steps of:
  (1) contacting the sample with the nanobody described in the second aspect of the invention;
  (2) detecting formation of antigen-antibody complex, wherein the formation of the complex indicated the presence of Her2 protein in the sample.

In the fifteenth aspect of invention, a method for treating a disease is provided. The method includes administering the nanobody described in the second aspect of invention or the immunoconjugate described in the seventh aspect of the invention to an object in need.

In another preferred embodiment, the object in need includes mammal, such as human.

In the sixteenth aspect of the invention, a Her2 protein detection reagent is provided, and the detection reagent comprises the immunoconjugate according to the seventh aspect of the invention and a detection acceptable carrier.

In another preferred embodiment, the conjugating part of the immunoconjugate is a diagnostic isotope.

In another preferred embodiment, the detection acceptable carrier is a non-toxic, inert aqueous carrier media.

In another preferred embodiment, the detection reagent is one or more reagents selected from the group consisting of isotope tracer, contrast agent, flow detection reagent, cellular immunofluorescence detection reagent, magnetic nanoparticles and imaging agent.

In another preferred embodiment, the detection reagent is a contrast agent, and the contrast agent also contains other preparations for radiography.

In another preferred embodiment, the contrast agent is a contrast agent for MRI (magnetic resonance imaging) or CT (computer X-ray tomography).

In another preferred embodiment, the imaging agent chelates two or more signals at the same time, such as Ga-68 and Gd for both PET/CT and MRI; or Tc-99m and fluorescence agent for both SPECT/CT and fluorescence detection.

In another preferred embodiment, the detection reagent is used for in vivo detection.

In another preferred embodiment, the dosage form of the detection reagent is either in a form of liquid or powder (e.g. water agent, injection, freeze-dried powder, tablet, oral agent, and aerosol).

In the 17th aspect of the invention, a kit for detecting Her2 molecules is provided. The kit contains the immunoconjugate described in the seventh aspect of the invention and specification.

In another preferred embodiment, the specification records that the kit is used to non-invasively detect the Her2 expression of the object to be tested.

In another preferred embodiment, the kit is used for the detection of tumors expressing Her2 protein (i.e. Her2 positive)

In the eighteenth aspect of the invention, a use of the immunoconjugate described in the seventh aspect of invention is provided for preparing a contrast agent for detecting Her2 molecules in vivo.

In another preferred embodiment, the detection is used for the diagnosis or prognosis of cancer.

In the nineteenth aspect of the invention, a CAR-T cell is provided. The CAR-T cell expresses chimeric antigen receptor CAR, and antigen binding domain of the CAR has the VHH chain as described in the first aspect of invention, or the nanobody described in the second aspect of invention.

In the twentieth aspect of the invention, a preparation is provided. The preparation contains the CAR-T cell as described in nineteenth aspect of invention, as well as a pharmaceutically acceptable carrier, diluent or excipient.

In another preferred embodiment, the preparation is a liquid preparation.

In another preferred embodiment, dosage form of preparation includes injection.

In another preferred embodiment, concentration of the CAR-T cells in the preparation is $1\times10^3$-$\times10^8$ cells/ml, preferably $1\times10^4$-$1\times10^7$ cells/ml.

It is to be understood that within the scope of the present disclosure, the above-described technical features of the present invention and the technical features specifically described in the following (e.g., examples) may be combined with each other to form a new or preferred technical solution, which will not be repeated herein due to the limited space.

DETAILED DESCRIPTION

Figure 1:
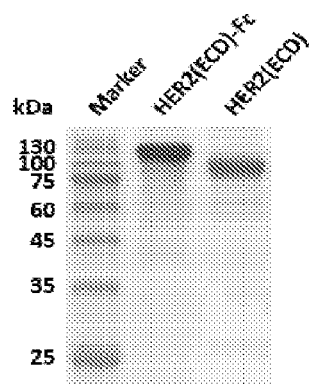
FIG. 1 shows SDS-PAGE diagram of antigen protein purification. Three electrophoresis lanes from left to right in FIG. 1 are nucleic acid molecular for reference, purified human Her2 (ECD)-Fc protein and the human Her2 (ECD) protein digested by TEV enzyme. The proteins above are both expressed by HEK293F cell.

Through extensive and in-depth research, the inventor successfully obtained a class of anti-Her2 nanobodies after numerous screening. Experimental results show that the Her2 nanobody obtained by the invention can effectively bind to Her2.

In particular, the human Her2 antigen protein was used to immunize a camel, thereby obtaining a gene library of nanobodies with high quality. The Her2 protein molecules were coated onto an ESLIA plate and exhibited correct spatial structure of Her2 protein. The antigens in such configuration were used to screen the gene library of nanobodies using phage display technology (phage display of a gene library from camel heavy chain antibodies) thereby obtaining genes of nanobodies with Her2 specificity. Then the genes were transferred into *E. coli* thereby obtaining the strains which can be effectively expressed in *E. coli* with high specificity.

The invention also discovered an immunoconjugate specifically suitable for detecting Her2 molecules for the first time. The immunoconjugate comprises a specific VHH chain of anti-Her2 nanobody and a radionuclide and can be used for non-invasive detection of Her2 expression in the subject to be tested. The immunoconjugate of invention has a small size and high specificity, making it suitable for systemic detection of primary and metastatic tumors. In addition, the immunoconjugate has high accuracy and low radiation dose.

In addition, the invention also provides an immunoconjugate which can effectively treat Her2 positive tumor.

As used herein, the terms "nanobody of the invention", "anti-Her2 nanobody of the invention" and "Her2 nanobody of the invention" are interchangeable, and all refer to nanobody that specifically recognize and bind to Her2 (including human Her2). The more preferable nanobody is one comprising a VHH chain of amino acid sequence as shown in SEQ ID NOs.:1-40.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the terms "single domain antibody (VHH)" and "nanobody" have the same meaning referring to a variable region of a heavy chain of an antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained. The variable regions of the heavy chain of the antibody are therefore cloned to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-folded configuration, joined by three CDRs which form a linking loop, and in some cases can form a partially β-folded structure. The CDRs in each chain are closely adjacent to the others by the FR regions and form an antigen-binding site of the nanobody with the CDRs of the other chain (see Kabat et al., NIH Publ. No. 91-3242, Volume I, pages 647-669. (1991)). The constant regions are not directly involved in the binding of the nanobody to the antigen, but they exhibit different effects or functions, for example, involving in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface marker or an antigen that binds to said anti-Her2 protein nanobody or the fragment thereof.

As used herein, the term "heavy chain variable region" and "$V_H$" can be used interchangeably.

As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above said heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to Her2 protein. They may or may not contain a starting methionine.

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure in which the β-sheets formed by the FRs therebetween are spatially close to each other, and the CDRs on the heavy chain and the CDRs on the corresponding light chain constitute the antigen-binding site of the nanobody. The amino acid sequences of the same type of nanobodies can be compared to determine which amino acids constitute the FR or CDR regions.

The variable regions of the heavy chains of the nanobodies of the invention become a particular interest because at least a part of them is involved in binding antigens. Thus, the present invention includes those molecules having a nanobody heavy chain variable region with a CDR, provided that their CDRs are 90% or more (preferably 95% or more, the most preferably 98% or more) identical to the CDRs identified herein.

The present invention includes not only intact nanobodies but also fragment(s) of immunologically active nanobody or fusion protein(s) formed from nanobodies with other sequences. Therefore, the present invention also includes fragments, derivatives and analogs of the nanobodies.

As used herein, the terms "fragment," "derivative," and "analog" refer to a polypeptide that substantially retains the same biological function or activity of a nanobody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6 His tag). According to the teachings herein, these fragments, derivatives, and analogs are within the scope of one of ordinary skill in the art.

The nanobody of the present invention refers to a polypeptide including the above CDR regions having Her2 protein binding activity. The term also encompasses variant forms of polypeptides comprising the above CDR regions that have the same function as the nanobodies of the invention. These variations include, but are not limited to, deletion insertions and/or substitutions of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the nanobodies of the invention.

The variant forms of the polypeptide include: homologous sequences, conservative variants, allelic variants, natural mutants, induced mutants, proteins encoded by DNAs capable of hybridizing with DNA encoding the nanobody of the present invention under high or low stringent conditions, and polypeptides or proteins obtained using antiserum against the nanobodies of the invention.

The invention also provides other polypeptides, such as a fusion protein comprising nanobodies or fragments thereof. In addition to almost full-length polypeptides, the present invention also includes fragments of the nanobodies of the invention. Typically, the fragment has at least about 50 contiguous amino acids of the nanobody of the invention, preferably at least about 50 contiguous amino acids, more preferably at least about 80 contiguous amino acids, and most preferably at least about 100 contiguous amino acids.

In the present invention, "a conservative variant of a nanobody of the present invention" refers to the polypeptides in which there are up to 10, preferably up to 8, more preferably up to 5, and most preferably up to 3 amino acids substituted by amino acids having analogical or similar properties, compared to the amino acid sequence of the nanobody of the present invention. These conservative variant polypeptides are preferably produced according to the amino acid substitutions in Table 1.

TABLE 1

| Original residue | Representative substitution | Preferable substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above nanobody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only under the identity between the two sequences at least over 90%, preferably over 95%. Also, polypeptides encoded by hybridizable polynucleotides have the same biological functions and activities as mature polypeptides.

The full-length nucleotide sequence of the nanobody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then connecting them. In addition, the coding sequence of the heavy chain and the expression tag (eg, 6His) can be fused together to form a fusion protein.

Once the concerned sequences have been obtained, the concerned sequences can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (or e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli*, *Streptomyces*, bacterial cells such as *Salmonella typhimurium*, fungal cells such as yeast, insect cells of *Drosophila* S2 or Sf9, animal cells of CHO, COS7, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$ method. The procedures used are well known in the art. Another method is to use $MgCl_2$. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods, utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultracentrifugation, molecular sieve chromatography (gel filtration), adsorption layer analysis, ion exchange chromatography, high performance liquid chromatography (HPLC), various other liquid chromatography techniques and the combinations thereof.

The antibodies of the invention may be used alone, or in combination with each other or in conjugated with a detectable marker (for diagnostic purposes), a therapeutic agent, a PK (protein kinase) modification moiety, or a combination thereof.

Detectable markers for diagnostic purposes include, but are not limited to: fluorescent or luminescent markers, radioactive markers, MRI (magnetic resonance imaging) or CT (computed tomography) contrast agents, or enzymes capable of producing detectable products.

Therapeutic agents that can be binded or conjugated to the nanobodies of the present invention include, but are not limited to: 1. Radionuclides; 2. Biological poisons; 3. Cytokines such as IL-2, etc.; 4. Gold nanoparticles/nanorods; 5. Viruses Particles; 6. Liposome; 7. Nano magnetic particles; 8. Drug activating enzymes (for example, DT-diaphorase (DTD) or biphenyl hydrolase-like protein (BPHL)); 10. Chemotherapeutic agents (for example, cisplatin) or any form of nanoparticles, etc.

Immunoconjugate

The invention also provides an immunoconjugate comprising:
(a) the VHH chain of the anti-Her2 nanobody as described in the first aspect of the invention, or the anti-Her2 nanobody as described in the second aspect of the invention; and
(b) a conjugating part selected from the group consisting of radionuclides, enzyme antibodies, cells, and a combination thereof.

In another preferred embodiment, the immunoconjugate is described in the seventh aspect of the invention.

The immunoconjugate of invention can be used for noninvasive detection of Her2 expression of the object to be tested. The immunoconjugate has small size and high specificity and is suitable for systemic detection of primary and metastatic tumors with high accuracy and low radiation dose.

Cytotoxic Agent

The conjugating part of the antibody immunoconjugate of invention includes: toxins, such as small molecular toxins or enzyme active toxins from bacteria, fungi, plant or animal, including their fragments and/or variants. Examples of cytotoxic agents include, but are not limited to: Auristatins (for example, Auristatin E, Auristatin F, MMAE and MMAF), chlortetracycline, metotanol, ricin, ricin A-chain, cobustatin, dokamicin, Dora statin, adriamycin, daunorubicin, paclitaxel, cisplatin, cc1065, ethidium bromide, mitomycin, etoposide, tenoposide, vincristine, vinblastine, colchicine, dihydroxyanthracnose diketone, actinomycin, diphtheria toxin, *Pseudomonas* exotoxin (PE) A, PE40, abrin, abrin A chain, modeccin A chain, α-Sarcina, gelonin, mitogellin, retstrictocin, phenomycin, enomycin, curicin, crocotin, calicheamicins, *Sapaonaria officinalis* inhibitor, as well as glucocorticoid and other chemotherapy agents. The conjugating part also includes radioisotopes such as At211, I131, I125, Y90, Re186, Re188, Sm153, Bi212 or 213, P32 and Lu (including Lu177). Antibodies can also be conjugated to anticancer prodrug activating enzymes that can convert prodrugs into their active forms.

The preferred small molecular drug is compound with high cytotoxicity, preferably is monomethylauristatin, galactomycin, medenin, and a combination thereof; more preferably is monomethylolastatin-E (MMAE), monomethylolastatin-D (MMAD), monomethylolastatin-F (MMAF), and a combination thereof.

Pharmaceutical Composition

The invention also provides a composition. Preferably, the composition is a pharmaceutical composition comprising the above antibody or active fragment or fusion protein or immunoconjugate thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind Her2 protein molecules and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned nanobodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 ng/kg body weight to about 50 mg/kg body weight per day, more preferably about 50 ng/kg body weight to about 1 mg/kg body weight or 10 µg/kg body weight to about 10 mg/kg body weight. In addition, the polypeptide or its conjugate of the invention may also be used with another therapeutic agent, such as antineoplastic agent or immunomodulatory.

When a pharmaceutical composition is used, a safe and effective amount of the immune-conjugate is administered to the mammal, wherein the safe and effective amount is usually at least about 10 ng/kg body weight, and in most cases, no more than about 50 mg/kg body weight, preferably the dose is about 50 ng/kg body weight to about 1 mg/kg body weight. Of course, factors such as the route of administration and the patient's health status should be considered to define the specific doses, all of which are within the skills of skilled physicians.

Nanobody with Markers

In a preferred embodiment of the invention, the nanobody carries detectable marker. More preferably, the marker is selected from the group consisting of isotope, colloidal gold marker, colored marker, and fluorescent marker.

Colloidal gold markers can be performed using methods known to those skilled in the art. In a preferred embodiment of the invention, the anti-Her2 nanobody is marked with colloidal gold to obtain a colloidal gold-marketed nanobody.

The anti-PD-L1 nanobody of the invention have very good specificity and high titer.

CAR-T Cell

As used herein, the terms "CAR-T cell", "CAR-T" and "CAR-T cell of the invention" refer to the CAR-T cell described in the nineteenth aspect of the present invention.

As used herein, chimeric antigen receptor (CAR) includes extracellular domain, optional hinge domain, transmembrane domain, and intracellular domain. Extracellular domain includes optional signal peptide and target-specific binding element (also known as antigen binding domain). Intracellular domain includes costimulatory molecules and zeta chain. Costimulatory signaling region comprises part of the intracellular domain of costimulatory molecules. Costimulatory molecules are the cell surface molecules needed for the effective response of lymphocytes to antigens, rather than antigen receptors or their ligands.

As used herein, "antigen binding domain" and "single chain antibody fragment" refer to Fab fragment, Fab' fragment, F (ab')$_2$ fragment, or single Fv fragment with antigen binding activity. Fv antibody contains variable region of heavy chain and variable region of the light chain of the antibody. Fv antibody has the smallest antibody fragment with antigen binding sites with no constant region. In general, Fv antibody also contains peptide junctions between VH and VL domains and can form the structures required for antigen binding. Antigen binding domain is usually scFv (single-chain variable fragment), which is preferably an amino acid chain sequence encoded by a nucleoside chain. As a preferred embodiment of the invention, the scFv includes the VHH chain described in the first aspect of the invention, or the nanobody described in the second aspect of the invention.

For both hinge domain and transmembrane region (transmembrane domain), CAR can be designed to comprise the transmembrane domain fused to the extracellular domain of CAR. In one embodiment, a transmembrane domain naturally associated with one of the domains in which the CAR is used. In some examples, transmembrane domains may be selected or modified by amino acid substitution to avoid binding such domains to the transmembrane domains of the same or different surface membrane proteins, thus minimizing interaction with other members of the receptor complex.

Junction can be incorporated between the extracellular domain and transmembrane domain of CAR or between cytoplasmic domain and transmembrane domain of CAR.

As used herein, the term "junction" usually refers to any oligopeptide or polypeptide that connects the transmembrane domain to the extracellular or cytoplasmic domain of the polypeptide chain. The junction may include 0-300 amino acids, preferably 2 to 100 amino acids and more preferably 3 to 50 amino acids.

When CAR is expressed in T cells, the extracellular domain can recognize a specific antigen and transduce the signal through the intracellular domain, causing cell activation and proliferation, cytotoxicity and secretion of cytokines such as IL-2 and IFN-γ. This also affects tumor cells, inhibit the tumor cells and induce apoptosis, and this also reduces or eliminates the tumor load in patients. Antigen binding domain is preferably fused with one or more intracellular domains from costimulatory molecules and Zeta chains.

Detection Method

The invention also relates to a method for detecting Her2 protein. The steps of the method are basically as follows: obtaining cell and/or tissue samples; dissolving the samples in a medium; and detecting the level of Her2 protein in the dissolved samples.

In the detection method of invention, the samples used do not have strict limitations, and a representative example is a cell-containing sample present in a cell preservation solution.

Kit

The invention also provides a kit containing an antibody (or a fragment thereof) or a detection board of invention. In a preferred embodiment of the present invention, the kit also includes a container, a usage manual, a buffer etc.

This invention also provides a detection kit for detecting the Her2 level, which includes an antibody for identifying the Her2 protein, a lysis medium for dissolving the sample, a general reagent and a buffer needed for detection, such as various buffer, detection markers, and detection substrates and so on. The detection kit is an in vitro diagnostic device.

The invention also provides a kit containing the immunoconjugate of invention. In a preferred embodiment of the present invention, the kit also includes a container, manual, isotope tracer and one or more reagents selected from the group consisting of: contrast agent, flow detection reagent, cellular immunofluorescence detection reagent, nanometer magnetic particle and imaging agent.

The preferred kit of the invention is an in vivo diagnostic kit, which is used for non-invasive detection of Her2 expression of the object to be tested.

Application

As mentioned above, the nanobody of invention has extensive biological application value and clinical application value. Its application involves various fields such as diagnosis and treatment of diseases related to Her2, basic medical research, biological research and so on. One preferred application is for clinical diagnosis and targeted treatment of Her2.

Major advantages of invention include:
(a) The nanobody of the invention has high specificity against human Her2 protein with correct spatial structure.
(b) The nanobody of the invention has a strong affinity.
(c) The nanobody of the invention is simple to produce
(d) The nanobody of invention can specifically bind to human Her2, and accumulate effectively in the tumor model with high expression of Her2 without competing with Trastuzumab or Pertuzumab. The nanobody of invention is very suitable for Her2 targeted cancer diagnosis and curative effect evaluation, as well as Her2 targeted in vivo radiotherapy for a new generation.

The present invention is further described in combination with specific embodiments. It should be understood that these examples are only for illustrating the present invention and are not intended to limit the scope of the present invention. The experimental methods that do not specify the specific conditions in the following examples are generally performed according to conventional conditions such as those described in Sambrook et al., Molecular Cloning: A Laboratory Manual (New York: Cold Spring Harbor Laboratory Press, 1989), or according to the conditions recommended by the manufacturer. Unless otherwise indicated, percentages and parts are percentages by weight and parts by weight.

Embodiment 1: Expression and Purification of Human Her2 Protein (1) Nucleotide sequence of human Her2 was synthesized in pCDNA3.1 (−) vector, and its extracellular domain sequence was subcloned into pFUSE-IgG1 vector. TEV restriction site was introduced at the C-terminal of hHer2 (ECD) for the preparation of a hHer2 (ECD) protein without Fe tag.
(2) The constructed pFUSE-IgG1-hHer2 (ECD) plasmid was extracted by an Omega plasmid Maxi kit.
(3) HEK293F cell was cultured to OD of $2.0\times10^6$ cells/mL.
(4) The plasmid was mixed with transfection reagent PEI at a ratio of 1:5, incubated for 10 min and then added into HEK293F cells. The transfected cell was incubated at 37° C., 6% $CO_2$ shaking bed incubator for 5-6 days.
(5) The supernatant of cells was collected and mixed with Protein A beads at room temperature for 1 h.
(6) The beads were washed with phosphate buffer (pH 7.0) and the protein was eluted with 0.1M pH 3.0 Glycine.
(7) The eluted protein was ultrafiltered into PBS and sampled for an SDS-PAGE test after yield measurement (the test results are shown in FIG. 1). The purity of antigen was greater than 95% and could be used for subsequent immunization.
(8) Then the Protein was digested with TEV enzyme and the untagged antigen protein Her2 (ECD) was obtained for subsequent antibody screening.

Figure 2:
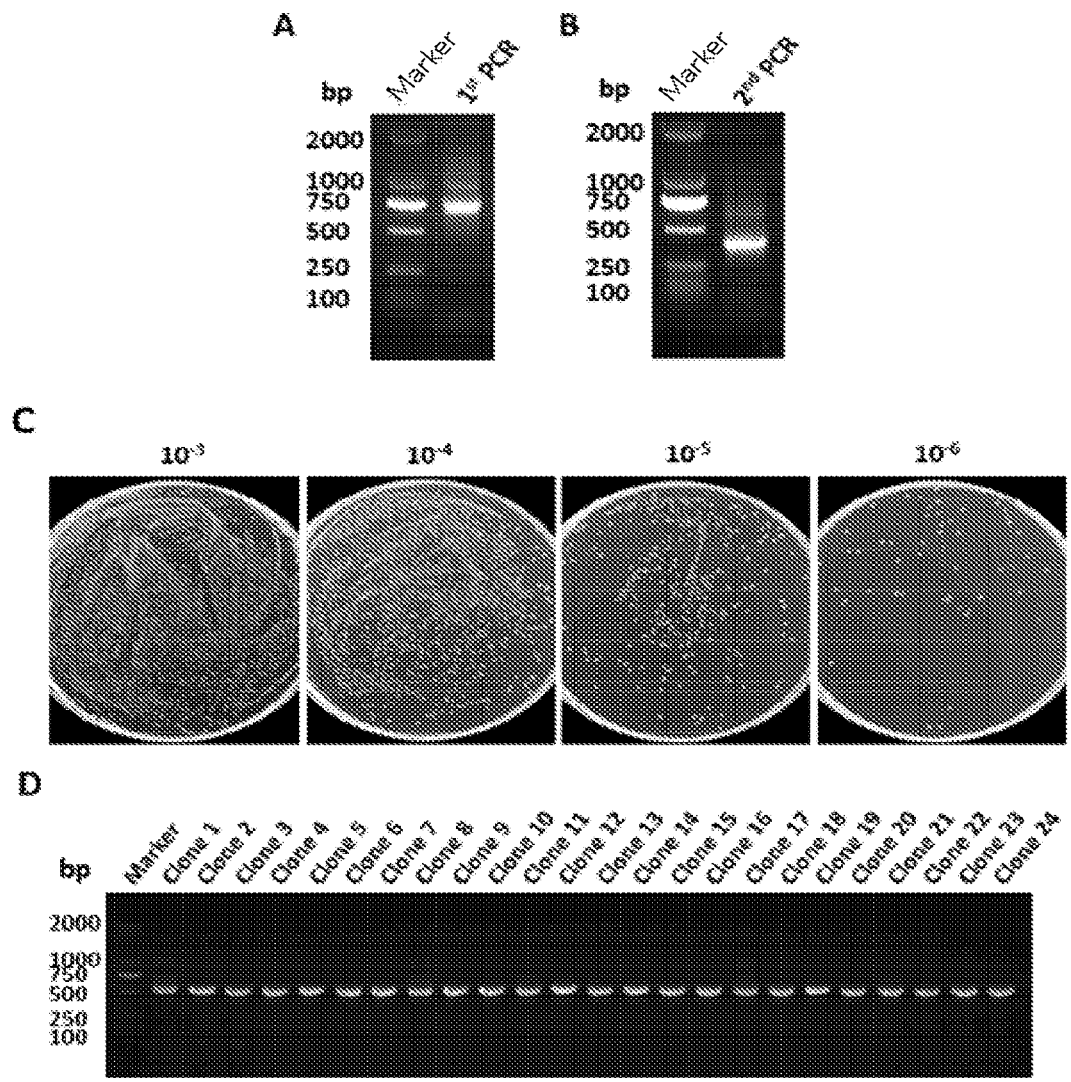
FIG. 2 shows a map of library construction and its quality inspection. Figure A shows the product of first PCR amplification, and the target band with a size of about 700 bp was tapped and recycled. Figure B shows the product of second PCR amplification, and the obtained VHH gene fragment is approximately 400 bp. Figure C shows the size of the constructed phage display library. The constructed library was coated onto a plate with gradient dilution. 1/5 of the clones was gradiently diluted. They were $10^3$ fold, $10^4$ fold, $10^5$ fold and $10^6$ fold dilutions. The number of clones was counted, and the size of the library was determined to be $2\times10^9$ CFU. Figure D shows the insertion rate of the library. 24 clones of the library were randomly selected for PCR identification. The DNA bands from left to right gel holes are indicated from the following: first is DNA molecular marker, and the rest are PCR products for detecting inserted fragments. The band of PCR product was about 500 bp and the detected VHH insertion rate of the library was 100%.

Embodiment 2: Construction of Anti-Her2 Nanobody Library (1) 1 mg hHer2 (ECD)-Fc antigen was mixed with Freund's adjuvant in equal volumes for the immunization of a Xinjiang camel once a week for a total of three times to stimulate B cells to express antigen-specific nanobody.
(2) 100 mL camel peripheral blood was collected after immunization for three times. RNA was extracted from lymphocytes in blood sample.
(3) The cDNA was synthesized and the VHH was amplified by nested PCR.
(4) 20 ug pMECs phage display vector (supplied by Biovector) and 10 ug VHH were digested with restriction endonuclease Pst I and Not L and two fragments were then ligated.
(5) The ligation products were transformed into TG1 cells with electroporation. Her2 nanobody library was constructed and the size of library was determined. Results are shown in FIG. 2C, the library was coated onto a plate. 1/5 of the clones was gradiently diluted. They were $10^3$ fold, $10^4$ fold, $10^5$ fold and $10^6$ fold dilutions. The number of clones was calculated. Size of the library was determined to be $2\times10^9$ CFU.
(6) At the same time, 24 clones were randomly selected for colony PCR detection. FIG. 2D shows the result of colony PCR and demonstrated that the insertion rate of the constructed library was 100%.

Embodiment 3: Screening and Identification of Her2 Nanobody

Screening of Antibody
(1) 10 μg Her2 (ECD)-Fc antigen (10 μg Fc in $NaHCO_3$ as control) dissolved in 100 mM $NaHCO_3$ (pH 8.2) was coupled to a NUNC plate then incubated at 4° C. overnight.
(2) 100 μL 0.1% BSA was added on the next day and blocked at room temperature for 2 h.

(3) After 2 hours, 100 μL bacteriophage (2×10$^{11}$ CFU nanobody phage display library from the immunized camel) was added and reacted at room temperature for 1 hour.

(4) The plate was washed 5 times with 0.05% PBS+ Tween-20 to remove non-specific bacteriophages.

Figure 3:
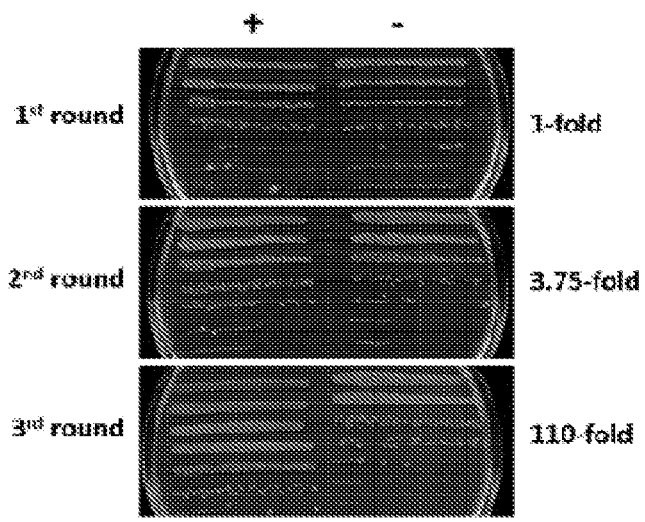
FIG. 3 shows screening and enrichment process of Her2 nanobody. The library was not enriched in the first round of panning, enriched 3.75 times in the second round of panning and 110 times in the third round of panning.

(5) 100 mM of triethanolamine was added to dissociate bacteriophages specifically bound to Her2. The bacteriophage was transformed to *Escherichia coli* TG1 cells in log phase and incubated at 37° C. for 1 h. The bacteriophages were generated and purified for the next round of screening. The screening process was repeated for 3 rounds. The enrichment results are shown in FIG. 3. 110× enrichment occurs after three rounds of biopanning process.

Phage-based enzyme-linked immunosorbent assay (ELISA) was used to screen specific single positive clone.

(5) The unbound antibody was washed off with PBST. Alkaline phosphatase chromogenic solution was added and the absorption value of each sample was read at 405 nm wavelength with spectrometer.

(6) When the OD value of the sample was over 3 times of the OD value of the control sample (Ratio+/−>3), the tested sample was determined to be a positive clone. A total of 486 positive clones were found from PE-ELISA and their ratios (Ratio: +/−) were between 3 and 30. Then all the positive clones were transferred to LA medium for plasmid extraction and sequencing. Because the number of sequencing results was large and most of the sequences were repetitive, only the corresponding ELISA results of the final 40 nanobodies were shown in Table 2.

TABLE 2

| Nanobody No. | 1 | 2 | 3 | 4 | 5 | 6 | 7 | 8 |
|---|---|---|---|---|---|---|---|---|
| A405+ | 1.7152 | 1.5341 | 1.3097 | 1.9694 | 1.1044 | 2.143 | 2.2361 | 2.5615 |
| A405− | 0.0769 | 0.0794 | 0.1009 | 0.0929 | 0.0871 | 0.0914 | 0.0816 | 0.0915 |
| Ratio(+/−) | 22.30 | 19.32 | 12.98 | 21.20 | 12.68 | 23.45 | 27.40 | 27.99 |
| Nanobody No. | 9 | 10 | 11 | 12 | 13 | 14 | 15 | 16 |
| A405+ | 2.1524 | 1.6302 | 1.8819 | 2.1761 | 2.2359 | 1.9576 | 2.2728 | 1.7853 |
| A405− | 0.0886 | 0.0728 | 0.0739 | 0.0851 | 0.0891 | 0.0804 | 0.087 | 0.0761 |
| Ratio(+/−) | 24.29 | 22.39 | 25.47 | 25.57 | 25.09 | 24.35 | 26.12 | 23.46 |
| Nanobody No. | 17 | 18 | 19 | 20 | 21 | 22 | 23 | 24 |
| A405+ | 1.8811 | 1.5904 | 1.7713 | 1.4735 | 2.0862 | 1.7769 | 1.7703 | 2.6757 |
| A405− | 0.0791 | 0.0829 | 0.0906 | 0.1439 | 0.1029 | 0.0833 | 0.1034 | 0.1127 |
| Ratio(+/−) | 23.78 | 19.18 | 19.55 | 10.24 | 20.27 | 21.33 | 17.12 | 23.74 |
| Nanobody No. | 25 | 26 | 27 | 28 | 29 | 30 | 31 | 32 |
| A405+ | 1.9731 | 1.8971 | 1.6555 | 1.857 | 1.4811 | 2.3129 | 1.6545 | 2.3609 |
| A405− | 0.0879 | 0.09 | 0.0808 | 0.0798 | 0.079 | 0.0966 | 0.0774 | 0.0934 |
| Ratio(+/−) | 22.45 | 21.08 | 20.49 | 23.27 | 18.75 | 23.94 | 21.38 | 25.28 |
| Nanobody No. | 33 | 34 | 35 | 36 | 37 | 38 | 39 | 40 |
| A405+ | 2.0527 | 2.2628 | 1.99 | 2.2236 | 2.095 | 2.1419 | 1.8579 | 1.5695 |
| A405− | 0.0965 | 0.1129 | 0.0947 | 0.1029 | 0.1067 | 0.0981 | 0.094 | 0.0824 |
| Ratio(+/−) | 21.27 | 20.04 | 21.01 | 21.61 | 19.63 | 21.83 | 17.76 | 19.05 |

(1) From the cell culture dishes containing the bacteriophages obtained after above 2-3 rounds of screening, 600 individual colonies were selected and inoculated into TB medium containing 100 μg/mL ampicillin (1 L of TB medium contains 2.3 g KH$_2$PO$_4$, 12.52 g K$_2$HPO$_4$, 12 g peptone, 24 g yeast extract, 4 mL glycerol). After growth to log phase, IPTG was added to a final concentration of 1 mM and cultured at 28° C. overnight.

(2) The crude antibodies were extracted by osmotic method, transferred to antigen coated ELISA plate and placed at room temperature for 1 hour.

(3) The unbound antibodies were washed off with PBST. Mouse anti-HA antibodies (purchased from Beijing Kangwei Century Biotechnology Co., Ltd.) was added and placed at room temperature for 1 hour.

(4) The unbound antibodies were washed off with PBST. Goat anti-mouse alkaline phosphatase labeled antibodies were added and placed at room temperature for 1 hour.

The nucleotide sequences of the 40 strains of nanobodies were shown in SEQ ID NO.: 1-40, respectively. The amino acid sequence of the VHH having number n is SEQ ID NO.: n, and the corresponding coding sequence is SEQ ID NO.: 40+n.

TABLE 3

| Number No. | Amino Acid Sequences SEQ ID NO.: | Nucleotide Sequences SEQ ID NO.: | 3 CDR locations (based on amino acid sequences) | | |
|---|---|---|---|---|---|
| | | | CDR1 | CDR2 | CDR3 |
| 1 | 1 | 41 | 26-35 | 51-57 | 96-112 |
| 2 | 2 | 42 | 26-35 | 51-57 | 96-112 |
| 3 | 3 | 43 | 26-35 | 51-57 | 96-112 |
| 4 | 4 | 44 | 26-35 | 51-57 | 96-112 |
| 5 | 5 | 45 | 26-35 | 51-57 | 96-107 |
| 6 | 6 | 46 | 26-35 | 51-57 | 96-114 |
| 7 | 7 | 47 | 26-35 | 51-57 | 96-114 |
| 8 | 8 | 48 | 26-35 | 51-57 | 96-112 |
| 9 | 9 | 49 | 26-35 | 51-57 | 96-112 |
| 10 | 10 | 40 | 26-35 | 51-57 | 96-112 |

TABLE 3-continued

| Number No. | Amino Acid Sequences SEQ ID NO.: | Nucleotide Sequences SEQ ID NO.: | 3 CDR locations (based on amino acid sequences) | | |
|---|---|---|---|---|---|
| | | | CDR1 | CDR2 | CDR3 |
| 11 | 11 | 41 | 26-35 | 51-57 | 96-112 |
| 12 | 12 | 42 | 26-35 | 51-57 | 96-112 |
| ... | ... | ... | ... | ... | ... |
| n | n | 40 + n | See sequence | See sequence | See sequence |

The sequences of 40 strains of nanobodies are as follows, where the three CDR regions of 40 strains of nanobodies are underlined.

```
SEQ ID NO. 1:
QVQLQESGGGSVQAGETLRLSCTASGFTFDDSDMGWYRQAPGNECELVSTISSDGSTYYADSVKGRF
TISQDNAKNTVYLQMNSLKPEDTAVYYCAAHPLHYELGTCAALDYWGRGTQVTVSS

SEQ ID NO. 2:
QVQLQESGGGSVQAGETLRLSCTASGFTFDDSDMGWYRQAPGNECELVSTISSDGSTYYADSVKGRF
TISQDNAKNAVYLQMNSLKPEDTAVYYCAAHPLHYELGTCAALDYWGRGTQVTVSS

SEQ ID NO. 3:
QVQLQESGGGSVQAGGSLRLSCTASGFTFDDSDVRWYRQAPGRECKLVSSISSDRSAYYEDSVKGRF
TISQDNAKNTVYLQMNSLKPEDTAVYYCAAHPLHYELGTCAALDYWGRGTQVTVSS

SEQ ID NO. 4:
QVQLQESGGGLVQPGGSLRLSCTASRFTFDDSDMAWYRQAPGNECELVSIISSDGSTYYADSVKGRF
TISLDNTKSTVYLQMNSLKPEDTAVYYCAAHPLHYELGTCAALDYWGRGTQVTVSS

SEQ ID NO. 5:
QVQLQESGGGSVQAGGSLRLSCTVSGFSFDDSDMGWYRRAPGNECELVSGISRDGSTYYADSVKGRF
TISQDNAKNWVYLQMNSLKPEDTAVYYCAAATYSDYVCDYWTQGTQVTVSS

SEQ ID NO. 6:
QVQLQESGGGSVQAGETLRLSCTASGFTFDDSDMGWYRQAPGNECELVSHISSDGSTYYADSVKGRF
TISQDNAKNTVFLQMNSLKPEDTAVYYCAADKDARGYELGTCESLDYWGRGTQVTVSS

SEQ ID NO. 7:
QVQLQESGGGSVQAGETLRLSCTASGFTFDDSDMGWYRQAPGNECELVSTISSDGSTYYADSVKGRF
TISQDNAKNTVYLQMNSLKPEDTAVYYCAADKDARGYELGTCESLDYWGRGTQVTVSS

SEQ ID NO. 8:
QVQLQESGGGSVQAGETLRLSCTASGFTFDESVMGWYRQAPGNECELVSTISSDGSTYYSNSVKGRF
TISQDNAKNTVYLQMNSLKPEDTAVYYCAADDHTYELGTCEALNYWGRGTQVTVSS

SEQ ID NO. 9:
QVQLQESGGGSVQAGETLRLSCTASGFTFDDSDMGWYRQAPGSECELVSTISSDGNTYYSNSVKGRF
TISQDNAKNTVYLQMNSLKPEDTAVYYCAADDQHYELGTCEALDYWGRGTQVTVSS

SEQ ID NO. 10:
QVQLQESGGGSVQAGETLKLSCTASGFTFDDSTMAWYRQAPGNECKLVSTISSDGSTYYADSVKGRF
TISQDNAKNTVYLQMNSLKPEDTAVYYCAADDQNYELGTCEALDYWGRGTQVTVSS

SEQ ID NO. 11:
QVQLQESGGGSVQAGETLRLSCTASGFTFDDSDMGWYRQAPGNECELVSHISSGGSTYYADSVKGRF
TISQDNAKNTVYLQMNSLKPEDTAVYYCAADGSNYELGTCAALDYWGRGTQVTVSS

SEQ ID NO. 12:
QVQLQESGGGSVQAGETLRLSCTASGFTFDDSDMGWYRQAPGNECELVSTISSDGSTYYADSVKGRF
TISQDNAKNTVYLQMNSLKPEDTAVYYCAADGHKYELGTCAALDYWGRGTQVTVSS

SEQ ID NO. 13:
QVQLQESGGGSVQAGETLRLSCTASGFTFDDSDMGWYRQAPGNECELVSTISADGSTFYADSVKGRF
TISQDNAKNTVYLQMNSLKPEDTAVYYCASPENEYELGTCEALDYWGQGTQVTVSS
```

SEQ ID NO. 14:
QVQLQESGGGSVQAGETLRLSCTASGFTFDDSDMGWYRQAPGNECELVSRISSDGSTYYADSVKGRF

TISQDNAKNTVYLQMNSLKPEDTAVYYCAALEWEYELGTCEALDYWGQGTQVTVSS

SEQ ID NO. 15:
QVQLQESGGGSVQAGGSLRLSCTASRFTFDDSDMGWYRQAPGNECELVSTISSDGATYYANSVKGRF

TISQDNAANTVYLQMNSLKPEDTAVYYCAALEWEYELGTCEALDYWGQGTQVTVSS

SEQ ID NO. 16:
QVQLQESGGGSVQAGGSLRLSCTASGFTFDDSDMVWYRQAPGNECELVSRISSDGSTYYADSVKGRF

TISQDNAKNTVYLQMNSLKPEDTAVYYCAALEWEYELGTCEALDYWGQGTQVTVSS

SEQ ID NO. 17:
QVQLQESGGGSVQAGGSLRLSCTASGFTFDDSDMGWYRQAPGNECELVSTISSDGSTYYADSVKGRF

TISQDNAKNTVYLQMNSLKPEDTAVYYCADVQIPYGLGTCESLDYWGRGTQVTVSS

SEQ ID NO. 18:
QVQLQESGGGSVQAGQTLRLSCTASGFTFDDSDMAWYRQAPGNECELVSKMRSDGSTYYADSVKGRF

TISQDNAKNTVYLQMNSLKPEDTAVYYCAEDLPYGLGTCTSLDYWGRGTQVTVSS

SEQ ID NO. 19:
QVQLQESGGGSVQAGGSLRLSCTASGFTFDDSDSDMGWYRQAPGNECELVSSISSDGSTYYADSVKG

RFTISQDNAKNTVYLQMNSLKPEDTAVYYCAAINSGYELGTCESLDYWGRGTQVTVSS

SEQ ID NO. 20:
QVQLQESGGGSVQAGGSLRLSCTASGFTFDDSVMGWFRKAPGNECELVSTISSDGSTYYADSVKGRF

TISQDNAKNTVYLQMNNLKPEDTAVYYCAAINSGYELGTCESLDYWGRGTQVTVSS

SEQ ID NO. 21:
QVQLQESGGGLVQPRGSLRLSCTASGFTFDDSDSDMGWYRQAPGNECELVSSISSDGSTYYADSVKG

RFTISQDNAKNTVYLQMNSLKPEDTAVYYCAAINSGYELGTCESLDYWGRGTQVTVSS

SEQ ID NO. 22:
QVQLQESGGGSVQAGGSLRLSCTASGFTFDDSDMGWYRQAPGNECELVSRISRDGTTYYADSVKGRF

TISQDNAKNTVYLQMNSLKPEDTAVYYCADINSGYELGTCESLDYWGRGTQVTVSS

SEQ ID NO. 23:
QVQLQESGGGSVQAGGSLKLSCSASGFTFDDTDMGWYRQAPGNECELVSTISSDGTTYYTDSVKGRF

TISQDNAKNTVYLQMNSLKPEDTAVYYCAAINSGYELGTCESLDYWGRGTQVTVSS

SEQ ID NO. 24:
QVQLQESGGGSVQAGETLRLSCTASGFTFDDSDSDMGWYRQAPGNECELVSSISSDGSTYYADSVKG

RFTISQDNAKNTVYLQMNSLKPEDTAVYYCAAINSGYELGTCESLDYWGRGTQVTVSS

SEQ ID NO. 25:
QVQLQESGGGSVQAGETLRLSCTASGFTFDDSDSDMGWYRQAPGNECELVSSISSDGSTYYADSVKG

RFTISQDNAKNTVYLQMNSPKPEDTAVYYCAAINSGYELGTCESLDYWGRGTQVTVSS

SEQ ID NO. 26:
QVQLQESGGGSVQAGETLRLSCTASGFTFDDSDMGWYRQAPGNECELVSSISSDGSTYYADSVKGRF

TISQDNAKNTVYLQMNSLKPEDTGVYYCAAEGHRYELGTCAALDYWGRGTQVTVSS

SEQ ID NO. 27:
QVQLQESGGGSVQAGETLRLSCTASGFTFDDSDMGWYRQAPGNECELVSTISSDGSTYYADSVKGRF

TISQDNAKNTVYLQMNSLKPEDTAVYYCAADHGGGYELGTCAALDYWGRGTQVTVSS

SEQ ID NO. 28:
QVQLQESGGGLVQPGGSLRLSCAASGFTFGDSGMGWYRQAPGNECELVSSVSSDGSTYYADSVKGRF

TISQDNAKNTVYLRMNSLKPEDTAVYYCAADDHKYELGTCEALDYWGRGTQVTVSS

SEQ ID NO. 29:
QVQLQESGGGSVQAGGSLRLSCTASGFTFDDLDMRWYRQAPGNECELVSIINSDGRTYYADSVKGRF

AISQNNAKNTVYLQMNSLKPEDTAVYYCAADQHRYGLGTCEALDYWGRGTQVTVSS

SEQ ID NO. 30:
QVQLQESGGGSVQAGETLRLSCTAS<u>GFTFDDSDMG</u>WYRQAPGNECELVST<u>ISSDGRT</u>YYADSVKGRF
AISQNNAKNTVYLQMNSLKPEDTAVYYC<u>AADQHRYGLGTCEALDY</u>WGRGTQVTVSS

SEQ ID NO. 31:
QVQLQESGGGSVQAGETLRLSCTAS<u>GFTFNDSNMG</u>WYRQAPGHECELVST<u>ISSDGST</u>YYADSVKGRF
TISQNNARNTVYLQMNSLKPEDTAVYYC<u>AGDWGYELGICTSLDY</u>WGQGTQVTVSS

SEQ ID NO. 32:
QVQLQESGGGSVQAGGSLRLSCTAS<u>GFTFDDVDMG</u>WYRQASGNECELVST<u>ISSDGST</u>YYADSVKGRF
TISQDNAKNTVYLQMNSLKPEDTAMYYC<u>AAARYSDYEGMCGY</u>WSQGTQVTVSS

SEQ ID NO. 33:
QVQLQESGGGSVQAGGSLRLSCTAS<u>GFTFDDVDMG</u>WYRQAPGNECELVST<u>ISSDGST</u>YYADSVKGRF
TISQDNAKNTVYLQMNSLKPEDTAMYYC<u>AAARYSDYEGMCGY</u>WSQGTQVTVSS

SEQ ID NO. 34:
QVQLQESGGGSVQAGGSLRLSCTVS<u>GFTFDDVDMG</u>WYRQAPGNECELVST<u>ISSDGST</u>YYADSVKGRF
TISQDNAKNTVYLQMNSLKPEDTAMYYC<u>AAARYSDYEGMCGY</u>WSQGTQVTVSS

SEQ ID NO. 35:
QVQLQESGGGLVQPGGSLRLSCAAS<u>GFTFDDVDMG</u>WYRQAPGNECELVST<u>ISSDGST</u>YYADSVKGRF
TISQDNAKNTVYLQMNSLKPEDTAMYYC<u>AAARYSDYEGMCGY</u>WSQGTQVTVSS

SEQ ID NO. 36:
QVQLQESGGGSVQAGESLRLSCRTS<u>GFSFDDVDMG</u>WYRQAPGNECELVST<u>ISSDGST</u>YYADSVKGRF
TISQDNAKNTVYLQMNSLKPEDTAMYYC<u>AAARYSDYEGMCGY</u>WSQGTQVTVSS

SEQ ID NO. 37:
QVQLQESGGGSVQAGETLRLSCTVS<u>GFTFDDADMG</u>WYRQAPGNQCELVST<u>ISSDGIT</u>YYADSVKGRF
TVSQDNAKNTVYLQMNSLKPEDTAMYYC<u>AAARYSDYEGMCGY</u>WSQGTQVTVSS

SEQ ID NO. 38:
QVQLQESGGGSVQAGGSLRLSCAAS<u>GFTYTGYCMG</u>WFRQAPGKEREGVAT<u>VDSDGDTS</u>YADSVKGRF
TISKDNAKNTLYLQMNSLKPEDTAMYYC<u>AADFSRWHLCSTSLATLGY</u>WGQGTQVTVSS

SEQ ID NO. 39:
QVQLQESGGGSVQAGGSLRLSCAAS<u>GYTYTGYCMG</u>WFRQAPGKEREGVAT<u>IDSDGDTS</u>YADSVKGRF
TISKDNAKNTLYLQMNSLKPEDTAMYYC<u>AADFRRWHLCSSSFREDGMDY</u>WGKGTQVTVSS

SEQ ID NO. 40:
QVQLQESGGGSVQAGETLRLSCAAS<u>GYTYTGYCMG</u>WFRQATGKEREGVAT<u>IDSDGDTT</u>YADSVKGRF
TISKDNGKNTLYLQMNSLKPEDTAMYYC<u>AADFRRWHLCSSSFQEYDMDY</u>WGKGTQVTVSS

SEQ ID NO. 41:
CAGGTGCAGCTGCAGGAGTCTGGAGGAGGCTCGGTGCAGGCTGGAGAGACTCTGAGACTCTCCTGTA
CAGCCTCTGGATTCACTTTTGATGATTCTGACATGGGCTGGTACCGCCAGGCTCCAGGGAATGAGTG
CGAGTTGGTCTCAACTATTAGTAGTGATGGTAGCACATACTATGCAGACTCCGTGAAGGGCCGATTC
ACCATCTCCCAAGACAACGCCAAGAACACGGTGTATCTGCAAATGAACAGCCTGAAACCTGAGGACA
CAGCCGTGTATTACTGTGCGGCACATCCCCTCCACTACGAGTTGGGTACGTGCGCGGCACTGGACTA
CTGGGGCCGGGGGACCCAGGTCACCGTCTCCTCA

SEQ ID NO. 42:
CAGGTGCAGCTGCAGGAGTCTGGGGGAGGCTCGGTGCAGGCTGGAGAGACTCTGAGACTCTCCTGTA
CAGCCTCTGGATTCACTTTTGATGATTCTGACATGGGCTGGTACCGCCAGGCTCCAGGGAATGAGTG
CGAGTTGGTCTCAACTATTAGTAGTGATGGTAGCACATACTATGCAGACTCCGTGAAGGGCCGATTC
ACCATCTCCCAAGACAACGCCAAGAACGCGGTGTATCTGCAAATGAACAGCCTGAAACCTGAGGACA
CAGCCGTGTATTACTGTGCGGCACATCCCCTCCACTACGAGTTGGGTACGTGCGCGGCACTGGACTA
CTGGGGCCGGGGGACCCAGGTCACCGTCTCCTCA

SEQ ID NO. 43:
CAGGTGCAGCTGCAGGAGTCTGGAGGAGGCTCGGTGCAGGCTGGAGGGTCTCTGAGACTCTCCTGTA

CAGCCTCTGGATTCACTTTTGATGATTCTGATGTGCGCTGGTACCGCCAGGCTCCAGGGCGTGAGTG

CAAGTTGGTCTCAAGTATTAGTAGTGACCGTAGCGCATACTATGAAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCACATCCCCTCCACTACGAGTTGGGTACGTGCGCGGCACTGGACTA

CTGGGGCCGGGGGACCCAGGTCACCGTCTCCTCA

SEQ ID NO. 44:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCGCATATTAGTAGTGATGGTAGCACATACTATGCAGACTCCGTGAAGGGCCGATTC

ACCATCTCCCAAGACAACGCCAAGAACACGGTCTTTCTGCAAATGAACAGCCTGAAACCTGAAGACA

CAGCCGTATATTACTGTGCGGCAGATAAAGACGCCCGCGGTTACGAGTTGGGTACGTGTGAGTCCCT

GGACTACTGGGGCCGGGGGACCCAGGTCACCGTCTCCTCA

SEQ ID NO. 45:
CAGGTGCAGCTGCAGGAGTCTGGGGGAGGCTCGGTGCAGGCTGGAGGGTCTCTGAGACTCTCCTGTA

CAGTCTCTGGATTCAGTTTCGATGATTCTGACATGGGCTGGTACCGCCGGGCTCCAGGGAATGAGTG

CGAGTTGGTCTCAGGTATCAGTAGAGATGGCAGCACATACTATGCAGACTCCGTGAAGGGCCGATTC

ACCATCTCCCAAGACAACGCCAAGAACTGGGTGTATCTGCAAATGAACAGCCTGAAACCTGAGGACA

CGGCCGTGTATTACTGTGCGGCAGCGACTTATAGCGACTATGTCTGTGACTACTGGACACAGGGGAC

CCAGGTCACCGTCTCCTCA

SEQ ID NO. 46:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCGCATATTAGTAGTGATGGTAGCACATACTATGCAGACTCCGTGAAGGGCCGATTC

ACCATCTCCCAAGACAACGCCAAGAACACGGTCTTTCTGCAAATGAACAGCCTGAAACCTGAAGACA

CAGCCGTATATTACTGTGCGGCAGATAAAGACGCCCGCGGTTACGAGTTGGGTACGTGTGAGTCCCT

GGACTACTGGGGCCGGGGGACCCAGGTCACCGTCTCCTCA

SEQ ID NO. 47:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATAAAGACGCCCGTGGCTACGAGTTGGGTACGTGTGAGTCCCT

GGACTACTGGGGCCGGGGGACCCAGGTCACCGTCTCCTCA

SEQ ID NO. 48:
CAGGTGCAGCTGCAGGAGTCTGGAGGAGGCTCGGTGCAGGCTGGAGAGACTCTGAGACTCTCCTGTA

CAGCCTCTGGATTCACTTTTGATGAATCTGTCATGGGCTGGTACCGCCAGGCTCCAGGGAATGAGTG

TGAGTTGGTCTCAACTATTAGTAGTGATGGTAGCACATACTATTCAAACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCCGATGATCACACCTACGAATTGGGTACCTGCGAGGCTCTCAACTA

CTGGGGCCGGGGGACCCAGGTCACCGTCTCCTCA

SEQ ID NO. 49:
CAGGTGCAGCTGCAGGAGTCTGGAGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAGTGAGTG

CGAGTTGGTCTCAACTATTAGTAGTGATGGTAACACCTACTATTCAAACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATGATCAGCACTACGAGTTGGGTACCTGCGAGGCTCTCGACTA

CTGGGGCCGGGGGACCCAGGTCACCGTCTCCTCA

SEQ ID NO. 50:
CAGGTGCAGCTGCAGGAGTCTGGAGGAGGCTCGGTGCAGGCTGGAGAGACTCTGAAACTCTCCTGTA

CAGCCTCTGGATTCACGTTTGATGATTCTACCATGGCCTGGTACCGCCAGGCTCCAGGGAATGAGTG

CAAGTTGGTGTCAACTATTAGTAGTGATGGGAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATGATCAGAACTACGAGTTAGGTACCTGCGAGGCTCTCGACTA

CTGGGGCCGGGGGACCCAGGTCACCGTCTCCTCA

SEQ ID NO. 51:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCACATATTAGTAGTGGTGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATGGGAGTAACTACGAATTGGGTACGTGCGCTGCCTTAGACTA

CTGGGGCCGGGGGACCCAGGTCACCGTCTCCTCA

SEQ ID NO. 52:
CAGGTGCAGCTGCAGGAGTCTGGAGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATGGGCATAAGTACGAGTTGGGTACGTGCGCTGCCTTAGACTA

CTGGGGCCGGGGGACCCAGGTCACCGTCTCCTCA

SEQ ID NO. 53:
CAGGTGCAGCTGCAGGAGTCTGGAGGAGGCTCGGTGCAGGCTGGAGAGACTCTGAGACTCTCCTGTA

CAGCCTCTGGATTCACTTTTGATGATTCTGATATGGGCTGGTACCGCCAGGCTCCAGGGAATGAGTG

CGAGTTGGTCTCAACTATTAGTGCTGATGGTAGCACATTCTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGTCCCCAGAGAATGAGTACGAATTGGGTACTTGCGAGGCCCTAGATTA

CTGGGGCCAGGGGACCCAGGTCACCGTCTCCTCA

SEQ ID NO. 54:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATCATGGCGGGGGGTACGAGTTGGGTACTTGTGCGGCCCTTGA

TTACTGGGGCCGGGGGACCCAGGTCACCGTCTCCTCA

SEQ ID NO. 55:
CAGGTGCAGCTGCAGGAGTCTGGGGGAGGCTCGGTGCAGGCTGGAGGGTCTCTGAGACTCTCCTGTA

CAGCCTCTAGATTCACTTTTGATGATTCTGACATGGGCTGGTACCGCCAGGCTCCAGGGAATGAGTG

CGAGTTGGTCTCGACTATTAGTAGTGATGGTGCCACATACTATGCAAACTCCGTGAAGGGCCGATTC

ACCATCTCCCAAGACAACGCCGCGAACACGGTATATCTACAAATGAACAGCCTGAAACCTGAGGACA

CAGCCGTTTATTACTGTGCGGCGTTAGAATGGGAATACGAATTGGGTACGTGCGAAGCCCTGGATTA

CTGGGGCCAGGGGACCCAGGTCACCGTCTCCTCA

SEQ ID NO. 56:
CAGGTGCAGCTGCAGGAGTCTGGGGGAGGCTCGGTGCAGGCTGGAGGGTCTCTGAGACTCTCCTGTA

CAGCCTCTGGATTCACTTTTGATGATTCTGACATGGTCTGGTACCGCCAGGCTCCAGGGAATGAGTG

CGAGTTGGTCTCACGTATTAGTAGTGATGGTAGCACATACTATGCAGACTCCGTGAAGGGCCGATTC

ACCATCTCCCAAGACAACGCCAAGAACACGGTATATCTACAAATGAACAGCCTGAAACCTGAGGACA

CAGCCGTTTATTACTGTGCGGCGTTAGAATGGGAATACGAATTGGGTACGTGCGAAGCCCTGGATTA

CTGGGGCCAGGGGACCCAGGTCACCGTCTCCTCA

SEQ ID NO. 57:
CAGGTGCAGCTGCAGGAGTCTGGGGGAGGCTCGGTGCAGGCTGGAGGGTCTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CGGCCGTGTATTACTGTGCGGACGTTCAGATCCCCTATGGGTTGGGTACCTGTGAGTCGTTGGACTA

CTGGGGCCGGGGACCCAGGTCACCGTCTCCTCA

SEQ ID NO. 58:
CAGGTGCAGCTGCAGGAGTCTGGGGGAGGCTCGGTGCAGGCTGGACAGACTCTGAGACTCTCCTGTA

CAGCCTCTGGATTCACTTTTGATGATTCTGACATGGCCTGGTACCGCCAGGCTCCAGGGAATGAGTG

CGAGTTGGTCTCAAAAATGCGTAGTGATGGTAGCACATACTATGCAGACTCCGTGAAGGGCCGCTTC

ACCATCTCCCAAGACAACGCGAAGAACACGGTGTATCTGCAAATGAACAGCCTGAAACCTGAGGACA

CAGCCGTGTATTACTGTGCGGAGGATTTGCCCTACGGGTTGGGTACTTGCACTTCCCTGGACTACTG

GGGCCGGGGACCCAGGTCACCGTCTCCTCA

SEQ ID NO. 59:
CAGGTGCAGCTGCAGGAGTCTGGGGGAGGCTCGGTGCAGGCTGGAGGGTCTCTGAGACTCTCCTGTA

CAGCCTCCGGATTCACTTTTGATGATTCTGATTCTGACATGGGCTGGTACCGCCAGGCTCCAGGGAA

CGAGTGCGAGTTGGTCTCATCTATTAGTAGTGATGGTAGCACATACTATGCAGACTCCGTGAAGGGC

CGATTCACCATCTCCCAAGACAACGCCAAGAACACGGTGTATCTGCAAATGAACAGCCTGAAACCTG

AGGACACAGCCGTGTATTACTGTGCAGCCATTAATTCTGGGTACGAGTTGGGTACTTGCGAGTCGTT

GGACTACTGGGGCCGGGGACCCAGGTCACCGTCTCCTCA

SEQ ID NO. 60:
CAGGTGCAGCTGCAGGAGTCTGGGGGAGGCTCGGTGCAGGCTGGAGGGTCTCTGCGACTCTCCTGTA

CAGCCTCTGGATTCACTTTTGATGATTCTGTGATGGGCTGGTTCCGGAAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAACCTGAAACCTGAGGACA

CGGCCGTGTATTACTGTGCAGCCATTAATTCTGGGTACGAGTTGGGTACTTGCGAGTCGTTGGACTA

CTGGGGCCGGGGACCCAGGTCACCGTCTCCTCA

SEQ ID NO. 61:
CAGGTGCAGCTGCAGGAGTCTGGAGGAGGCTTGGTCCAGCCTAGGGGGTCTCTGAGACTCTCCTGTA

CAGCCTCTGGATTCACTTTTGATGATTCTGATTCTGACATGGGCTGGTACCGCCAGGCTCCAGGGAA

CGAGTGCGAGTTGGTCTCATCTATTAGTAGTGATGGTAGCACATACTATGCAGACTCCGTGAAGGGC

CGATTCACCATCTCCCAAGACAACGCCAAGAACACGGTGTATCTGCAAATGAACAGCCTGAAACCTG

AGGACACAGCCGTGTATTACTGTGCAGCCATTAATTCTGGGTACGAGTTGGGTACTTGCGAGTCGTT

GGACTACTGGGGCCGGGGGACCCAGGTCACCGTCTCCTCA

SEQ ID NO. 62:
CAGGTGCAGCTGCAGGAGTCTGGGGGAGGCTCGGTGCAGGCTGGAGGGTCTCTGAGACTCTCCTGTA

CAGCCTCTGGATTCACTTTTGATGATTCTGACATGGGCTGGTACCGCCAGGCTCCAGGGAATGAGTG

CGAGTTGGTCTCACGTATTAGTCGTGATGGTACCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGACATTAATTCTGGGTACGAGTTGGGTACTTGCGAGTCGTTGGACTA

CTGGGGCCGGGGGACCCAGGTCACCGTCTCCTCA

SEQ ID NO. 63:
CAGGTGCAGCTGCAGGAGTCTGGGGGAGGCTCGGTGCAGGCTGGAGGGTCTCTGAAACTCTCCTGTT

CAGCCTCTGGATTCACTTTTGATGATACTGACATGGGCTGGTACCGCCAGGCTCCAGGGAATGAGTG

CGAGTTGGTCTCAACTATTAGTAGTGATGGTACCACATACTATACAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCAGCCATTAATTCTGGGTACGAGTTGGGTACTTGCGAGTCGTTGGACTA

CTGGGGCCGGGGGACCCAGGTCACCGTCTCCTCA

SEQ ID NO. 64:
CAGGTGCAGCTGCAGGAGTCTGGAGGAGGCTCGGTGCAGGCTGGAGAGACTCTGAGACTCTCCTGTA

CAGCCTCCGGATTCACTTTTGATGATTCTGATTCTGACATGGGCTGGTACCGCCAGGCTCCAGGGAA

CGAGTGCGAGTTGGTCTCATCTATTAGTAGTGATGGTAGCACATACTATGCAGACTCCGTGAAGGGC

CGATTCACCATCTCCCAAGACAACGCCAAGAACACGGTGTATCTGCAAATGAACAGCCTGAAACCTG

AGGACACAGCCGTGTATTACTGTGCAGCCATTAATTCTGGGTACGAGTTGGGTACTTGCGAGTCGTT

GGACTACTGGGGCCGGGGGACCCAGGTCACCGTCTCCTCA

SEQ ID NO. 65:
CAGGTGCAGCTGCAGGAGTCTGGGGGAGGCTCGGTGCAGGCTGGAGAGACTCTGAGACTCTCCTGTA

CAGCCTCCGGATTCACTTTTGATGATTCTGATTCTGACATGGGCTGGTACCGCCAGGCTCCAGGGAA

CGAGTGCGAGTTGGTCTCATCTATTAGTAGTGATGGTAGCACATACTATGCAGACTCCGTGAAGGGC

CGATTCACCATCTCCCAAGACAACGCCAAGAACACGGTGTATCTGCAAATGAACAGCCCGAAACCTG

AGGACACAGCCGTGTATTACTGTGCAGCCATTAATTCTGGGTACGAGTTGGGTACTTGCGAGTCGTT

GGACTACTGGGGCCGGGGGACCCAGGTCACCGTCTCCTCA

SEQ ID NO. 66:
CAGGTGCAGCTGCAGGAGTCTGGAGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAAGTATCAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGGCGTGTATTACTGTGCGGCAGAGGGGCACCGTTACGAGTTGGGTACGTGTGCAGCGTTAGACTA

CTGGGGCCGGGGGACCCAGGTCACCGTCTCCTCA

SEQ ID NO. 67:
CAGGTGCAGCTGCAGGAGTCTGGAGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCAACTATTAGTAGTGATGGTAGCACATACTATGCAGACTCCGTGAAGGGCCGATTC

ACCATCTCCCAAGACAACGCCAAGAACACGGTGTATCTGCAAATGAACAGCCTGAAACCTGAGGACA

CAGCCGTGTATTACTGTGCGGCAGATGGGCATAAGTACGAGTTGGGTACGTGCGCTGCCTTAGACTA

CTGGGGCCGGGGGACCCAGGTCACCGTCTCCTCA

SEQ ID NO. 68:
CAGGTGCAGCTGCAGGAGTCTGGAGGAGGCTTGGTGCAGCCTGGGGGGTCTCTGAGACTCTCCTGTG

CAGCCTCTGGATTCACTTTTGGTGATTCTGGCATGGGCTGGTACCGCCAGGCTCCAGGGAATGAGTG

CGAGTTGGTCTCAAGTGTGAGTAGTGATGGTAGCACATACTATGCAGACTCCGTGAAGGGCCGATTC

ACCATCTCCCAAGACAACGCCAAGAACACGGTGTATCTGCGAATGAACAGCCTGAAACCTGAGGACA

CAGCCGTGTATTACTGTGCGGCAGATGATCACAAGTACGAATTGGGTACCTGCGAGGCTCTCGACTA

CTGGGGCCGGGGGACCCAGGTCACCGTCTCCTCA

SEQ ID NO. 69:
CAGGTGCAGCTGCAGGAGTCTGGAGGAGGCTCGGTGCAGGCTGGAGGGTCTCTGAGACTCTCCTGTA

CAGCCTCTGGATTCACTTTTGATGATCTTGACATGCGCTGGTACCGCCAGGCTCCAGGGAATGAGTG

CGAGTTGGTCTCAATTATTAATAGTGATGGTAGAACATACTATGCAGACTCCGTGAAGGGCCGATTC

GCCATCTCCCAGAACAACGCCAAAAACACGGTGTATCTGCAAATGAACAGCCTGAAACCTGAGGACA

CAGCCGTGTATTACTGTGCGGCAGATCAACACCGCTACGGATTGGGTACGTGCGAGGCCTTAGACTA

CTGGGGCCGGGGGACCCAGGTCACCGTCTCCTCA

SEQ ID NO. 70:
CAGGTGCAGCTGCAGGAGTCTGGGGGAGGCTCGGTGCAGGCTGGAGAGACTCTGAGACTCTCCTGTA

CAGCCTCTGGATTCACTTTTGATGATTCTGACATGGGCTGGTACCGCCAGGCTCCAGGGAATGAGTG

CGAGTTGGTCTCTACTATTAGTAGTGATGGTAGAACATACTATGCAGACTCCGTGAAGGGCCGATTC

GCCATCTCCCAGAACAACGCCAAAAACACGGTGTATCTGCAAATGAACAGCCTGAAACCTGAGGACA

CAGCCGTGTATTACTGTGCGGCAGATCAACACCGCTACGGATTGGGTACGTGCGAGGCCTTAGACTA

CTGGGGCCGGGGGACCCAGGTCACCGTCTCCTCA

SEQ ID NO. 71:
CAGGTGCAGCTGCAGGAGTCTGGAGGAGGCTCGGTGCAGGCTGGAGAGACTCTGAGACTCTCCTGTA

CAGCCTCTGGATTCACTTTTAATGATTCTAACATGGGGTGGTACCGCCAGGCTCCAGGGCATGAGTG

CGAATTGGTCTCAACTATTAGTAGCGATGGTAGCACATACTATGCAGACTCCGTGAAGGGCCGATTC

ACCATCTCCCAAAACAACGCCAGGAACACCGTGTATCTGCAAATGAACAGCCTGAAACCTGAGGACA

CAGCCGTGTATTACTGTGCGGGAGACTGGGGCTACGAGTTGGGTATTTGCACCTCACTAGACTACTG

GGGCCAGGGGACCCAGGTCACCGTCTCCTCA

SEQ ID NO. 72:
CAGGTGCAGCTGCAGGAGTCTGGAGGAGGCTCGGTGCAGGCTGGAGGGTCTCTGAGACTCTCCTGTA

CAGCCTCTGGATTCACTTTTGATGATGTTGACATGGGCTGGTACCGCCAGGCTTCAGGGAATGAGTG

CGAGTTGGTCTCGACTATTAGTAGTGATGGTAGTACATACTATGCAGACTCCGTGAAGGGCCGATTC

ACCATCTCCCAAGACAACGCCAAGAACACGGTATATCTGCAAATGAACAGCCTGAAACCTGAGGACA

-continued

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 73:
CAGGTGCAGCTGCAGGAGTCTGGAGGAGGCTCGGTGCAGGCTGGAGGGTCTCTGAGACTCTCCTGTA

CAGCCTCTGGATTCACTTTTGATGATGTTGACATGGGCTGGTACCGCCAGGCTCCAGGGAATGAGTG

CGAGTTGGTCTCAACTATTAGTAGTGATGGTAGTACATACTATGCAGACTCCGTGAAGGGCCGATTC

ACCATCTCCCAAGACAACGCCAAGAACACGGTATATCTGCAAATGAACAGCCTGAAACCTGAGGACA

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 74:
CAGGTGCAGCTGCAGGAGTCTGGGGGAGGCTCGGTGCAGGCTGGAGGGTCTCTGAGACTCTCCTGTA

CAGTCTCTGGATTCACTTTTGATGATGTTGACATGGGCTGGTACCGCCAGGCTCCAGGGAATGAGTG

CGAGTTGGTCTCAACTATTAGTAGTGATGGTAGTACATACTATGCAGACTCCGTGAAGGGCCGATTC

ACCATCTCCCAAGACAACGCCAAGAACACGGTATATCTGCAAATGAACAGCCTGAAACCTGAGGACA

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 75:
CAGGTGCAGCTGCAGGAGTCTGGAGGAGGCTTGGTGCAGCCTGGGGGGTCTCTGAGACTCTCCTGTG

CAGCCTCTGGATTCACTTTTGATGATGTTGACATGGGCTGGTACCGCCAGGCTCCAGGGAATGAGTG

CGAGTTGGTCTCAACTATTAGTAGTGATGGTAGTACATACTATGCAGACTCCGTGAAGGGCCGATTC

ACCATCTCCCAAGACAACGCCAAGAACACGGTATATCTGCAAATGAACAGCCTGAAACCTGAGGACA

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 76:
CAGGTGCAGCTGCAGGAGTCTGGAGGAGGCTCGGTGCAGGCTGGAGAGAGTCTGAGACTCTCCTGTA

GAACCTCTGGATTCAGTTTTGATGATGTTGACATGGGCTGGTACCGCCAGGCTCCAGGGAATGAGTG

CGAGTTGGTCTCAACTATTAGTAGTGATGGTAGTACATACTATGCAGACTCCGTGAAGGGCCGATTC

ACCATCTCCCAAGACAACGCCAAGAACACGGTATATCTGCAAATGAACAGCCTGAAACCTGAGGACA

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 77:
CAGGTGCAGCTGCAGGAGTCTGGAGGAGGCTCGGTGCAGGCTGGAGAGACTCTGAGACTCTCCTGTA

CAGTCTCTGGATTCACTTTTGATGATGCTGACATGGGCTGGTACCGCCAGGCTCCAGGGAATCAGTG

CGAGTTGGTCTCAACTATTAGTAGTGATGGTATCACATACTATGCAGACTCCGTGAAGGGCCGATTC

ACCGTCTCCCAAGACAACGCCAAGAACACGGTATATCTGCAAATGAACAGCCTGAAACCTGAGGACA

CGGCCATGTATTACTGTGCGGCAGCCCGCTATAGCGACTATGAAGGGATGTGCGGTTACTGGAGCCA

GGGGACCCAGGTCACCGTCTCCTCA

SEQ ID NO. 78:
CAGGTGCAGCTGCAGGAGTCTGGAGGAGGCTCGGTGCAGGCTGGAGGGTCTCTGAGACTCTCCTGTG

CAGCCTCTGGATTTACCTACACTGGCTACTGCATGGGCTGGTTCCGCCAGGCTCCAGGGAAGGAGCG

CGAGGGGGTCGCAACGGTTGATAGTGATGGTGACACAAGCTACGCAGACTCCGTGAAGGGCCGATTC

ACCATCTCCAAAGACAACGCCAAGAACACTCTGTATCTGCAAATGAACAGCCTGAAACCTGAGGACA

CTGCCATGTACTACTGTGCGGCAGATTTTTCGCGGTGGCACCTATGTTCAACAAGCCTAGCTACCTT

GGGTTACTGGGGCCAGGGGACCCAGGTCACCGTCTCCTCA

SEQ ID NO. 79:
CAGGTGCAGCTGCAGGAGTCTGGAGGAGGCTCGGTGCAGGCTGGAGGATCTCTGAGACTCTCCTGTG

CAGCCTCTGGATACACCTACACTGGCTACTGCATGGGCTGGTTCCGCCAGGCTCCAGGGAAGGAGCG

CGAGGGGGTCGCAACTATTGATAGTGATGGTGACACAAGCTACGCAGACTCCGTGAAGGGCCGATTC

ACCATCTCCAAAGACAACGCCAAGAACACTCTGTATCTGCAAATGAACAGCCTGAAACCTGAGGACA

CTGCCATGTACTACTGTGCGGCAGACTTTCGCCGCTGGCACCTATGTAGTAGTTCGTTTCGGGAAGA

CGGCATGGACTACTGGGGCAAAGGAACCCAGGTCACCGTCTCCTCA

SEQ ID NO. 80:
CAGGTGCAGCTGCAGGAGTCTGGGGGAGGCTCGGTGCAGGCTGGAGAGACTCTGAGACTCTCCTGTG

CAGCCTCTGGATACACCTACACTGGCTACTGCATGGGCTGGTTCCGCCAGGCTACAGGGAAGGAGCG

CGAGGGGGTCGCAACTATTGATAGTGATGGAGACACAACCTACGCAGACTCCGTGAAGGGCCGATTC

ACCATCTCCAAAGACAACGGCAAGAACACTCTGTATCTGCAAATGAACAGCCTGAAACCTGAGGACA

CTGCCATGTACTACTGTGCGGCAGACTTTCGCCGCTGGCACCTATGTAGTAGCTCGTTTCAGGAGTA

CGACATGGACTACTGGGGCAAAGGAACCCAGGTCACCGTCTCCTCA

Embodiment 4: Expression and Purification of Nanobodies in Host Strain *Escherichia coli*

(1) For the clones obtained by sequencing analysis in embodiment 3 (7 nanobodies were randomly selected), the corresponding plasmids were electrotransformed into *E. coli* WK6 and coated on LA+glucose (i.e., containing ampicillin and glucose) culture plate. The plates were incubated overnight at 37° C.
(2) Single colony was selected and inoculated in 5 mL of LB medium containing ampicillin and cultured overnight at 37° C. on shaker.
(3) 1 mL overnight cultured strain was inoculated to 330 mL TB culture medium and incubated at 37° C. IPTG was added when OD value reached 0.6-1 and the culture was cultured overnight at 28° C. on shaker.
(4) The culture was centrifuged and the strains were collected.
(5) The crude extract of antibody was extracted by osmotic method.
(6) Purified nanobody was prepared by nickel column ion affinity chromatography.

Figure 4:
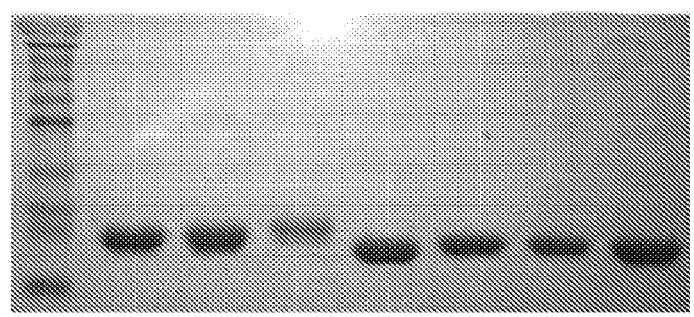
FIG. 4 shows purification result of Her2 nanobodies. Nanobodies was prepared and purified in one step by ion affinity chromatography with nickel column. Purity of the nanobodies are more than 95%.

The purification results were shown in FIG. 4. Through the purification process, the purity of anti-Her2 nanobody reached more than 95%.

Embodiment 5: Identification of Nanobody Affinity to Her2 of Different Species by Enzyme-Linked Immunosorbent Assay (ELISA)

(1) The human and mouse HER2 antigen protein was coated and added, then incubated overnight at 4° C.
(2) Next day, samples were washed with PBST for 3 times. 1% BSA was then added and blocked at room temperature for 2 hours.
(3) Purified nanobody was gradiently diluted and placed at room temperature with the coated Her2 antigen for 1 hour.
(4) Unbound antibodies were washed off with PBST. Mouse anti-HA antibody was then added, and samples were placed at room temperature for 1 hour.
(5) Unbound antibodies were washed off with PBST. Goat anti-mouse alkaline phosphatase labeled antibodies was then added. Samples were placed at room temperature for 1 hour.
(6) Unbound antibodies were washed off with PBST and alkaline phosphatase chromogenic solution was added. The absorption value was read at 405 nm wavelength via ELISA instrument, and the specificity of the nanobody was judged according to the absorption value.

Figure 5:
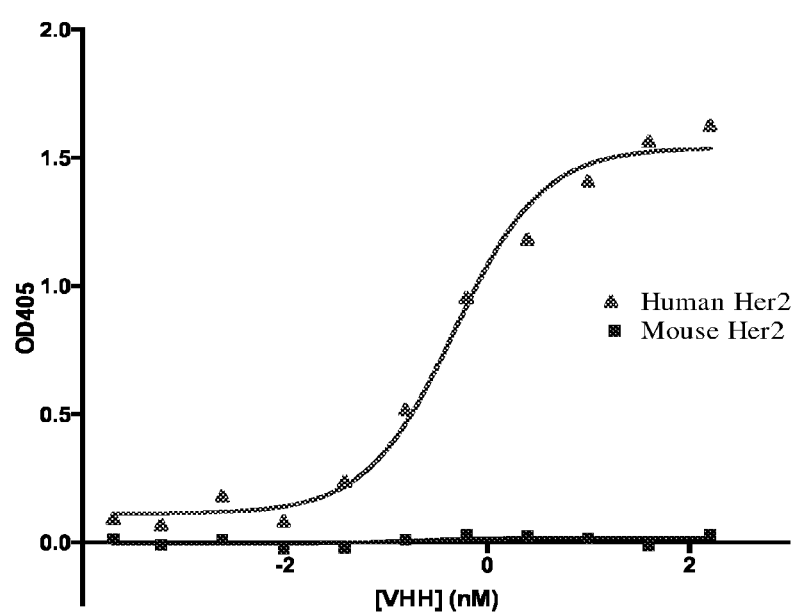
FIG. 5 shows affinity of Her2 nanobody to Her2 of different species. Nanobody reacted with human and mouse antigen protein Her2 at different gradient concentrations. Results showed that the nanobody only bound to human Her2.

The detection results are shown in FIG. 5. The nanobody of the current invention only binds to human Her2.

Embodiment 6: Detection of Nanobody Binding to Cells Via Flow Cytometry (1) Cell types: BT474 and MDA-MB-231. Cells were washed twice with PBS.
(2) Nanobody was diluted to 0.1 ug/ul with PBS
(3) Cells were divided into 96-well plates after washing, where number of cells per sample was $3\times10^5$. The dilute nanobodies were then added to each well, mixed and placed at 4° C. for 20 min.
(4) Cells were washed twice with PBS and resuspended with 100 uL PBS. 1 mL Mouse anti-HA Alexa Fluor488 labeled antibody was then added to each sample, mixed and placed at 4° C. for 20 min.
(5) Cells were washed twice with PBS and then resuspended to the flow tube with 300 uL PBS. Samples were kept on ice in dark condition. Detection was held via machine.

The results show that in the cell line with high expression of Her2 (BT474), the positive rate of nanobody of the invention is >99%, and in the cell line with low expression of Her2 (MDA-MB-231), the positive rate of nanobody is 6-14%. The difference between the two is at least about 6 times. This further suggests that the nanobody of invention has very excellent specificity against Her2. The results of some nanobodies are shown in Table 4.

TABLE 4

| Antibody no. | BT474 | MDA-MB-231 |
| --- | --- | --- |
| 9 | 99.8% | 9.5% |
| 10 | 99.7% | 10.6% |

TABLE 4-continued

| Antibody no. | BT474 | MDA-MB-231 |
|---|---|---|
| 13 | 99.9% | 14.2% |
| 17 | 99.9% | 12.3% |
| 22 | 99.7% | 5.8% |
| 23 | 99.9% | 11.5% |
| 26 | 99.9% | 16.7% |

Embodiment 7: Biacore 3K Affinity and Competitive Determination of Trastuzumab and Pertuzumab (1) Immobilization: the stationary phase antigen protein Her2 was immobilized on the surface of CM-5 sensor chip by carboxyl amino reaction.
(2) Binding: The nanobody was diluted into different concentrations using HBS buffer. Binding process of nanobody with Trastuzumab or Pertuzumab monoclonal antibody or with antigen alone was observed.
(3) Chip regeneration: when next antibody was determined, the chip was washed with 10 mM Glycine. Results show that the affinity of the nanobody of the invention to Her2 is above the level of nanomole concentration and does not compete with Trastuzumab or Pertuzumab to bind Her2. The data of some nanobodies is shown in Table 5.

TABLE 5

| Antibody no. | $K_{on}$(1/Ms) | $K_{off}$(1/s) | KD (M) | Competition with Trastuzumab | Competition with Pertuzumab |
|---|---|---|---|---|---|
| 9 | 1.11E+06 | 3.97E−03 | 3.60E−09 | — | — |
| 10 | 7.06E+05 | 4.57E−03 | 6.47E−09 | — | — |
| 13 | 1.27E+06 | 1.50E−03 | 1.18E−09 | — | — |
| 17 | 6.31E+05 | 4.21E−03 | 6.68E−09 | — | — |
| 22 | 9.57E+05 | 1.90E−03 | 1.98E−09 | — | — |
| 23 | 6.82E+05 | 2.55E−03 | 3.73E−09 | — | — |
| 26 | 8.57E+05 | 1.12E−03 | 1.31E−09 | — | — |

Embodiment 8. Isolation, Purification and SPECT Imaging Scanning of I-125 Labeled Nanobody (1) 150 μL of nanobody was added into 100 μL of 0.02 mol/L pH7.4 phosphate buffer solution and 50 μL of Na125I solution. The solution was mixed and 20 μL of 5 mg/mL chloramine T solution was added. The solution was incubated on a mixer for 70 s at room temperature. 200 μL sodium metabisulfite solution (5 mg/mL) was then added and incubated for minutes.

(2) Nanobody was isolated with PD10 column and eluted using 0.02 mol/L pH7.4 phosphate buffer solution. 10 drops were collected per tube. The radiopurity of I-125 labeled nanobody was identified by paper chromatography.
(3) Estrogen tablets were implanted subcutaneously on the right back of NOD/SCID mice the day before cell inoculation. $1\times10^7$ Her2 high expression tumor cells (BT474) were inoculated in right mammary fat pad. The tumor was used for formal experimental study when the size grown to 150-200 mm³.
(4) Tumor-bearing mice were anesthetized with isoflurane. I125 labeled nanobody (~50 ug, 5MBq) was intravenously injected into the tail of the mice.
(5) Scanning was performed 30 min after administration with acquisition method of static 15 min SPECT and medium resolution systemic CT.

Result shows that a plurality of nanobodies of invention can effectively accumulate in the tumor model with high expression of Her2 and can be applied to the diagnosis and treatment of cancer. At the same time, non-binding antibodies can be quickly removed from the blood through the kidneys and bladder, reducing the radiation dose of the body.

Figure 6:
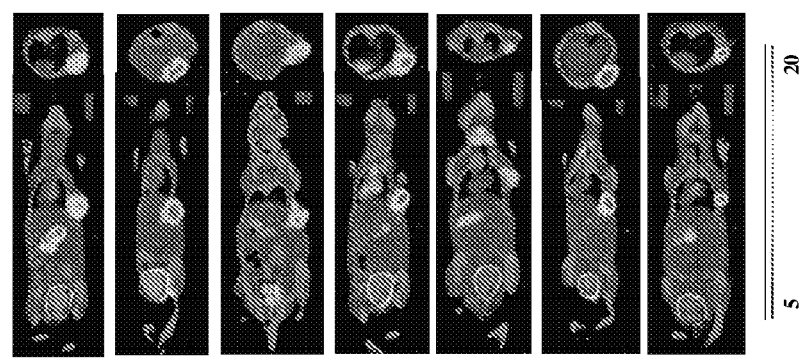
FIG. 6 shows SPECT-CT imaging results of I-125 labeled HER-2 nanobody in tumor-bearing mice with high expression of Her2. Results showed that several nanobodies could effectively accumulate in highly expressed tumors of Her2, and non-binding antibodies could be quickly removed from the blood through kidney and bladder.

The 30 min SPECT scan images and biodistribution data in vivo of some nanobodies in tumor-bearing mice are shown in FIG. 6 and Table 6.

TABLE 6

| | ID %/g | | | | | | |
|---|---|---|---|---|---|---|---|
| Organ | 9 | 10 | 13 | 17 | 22 | 23 | 26 |
| Heart | 6.7 ± 0.1 | 7.1 ± 0.9 | 8.3 ± 0.2 | 6.9 ± 0.4 | 5.6 ± 0.7 | 6.5 ± 0.4 | 6.2 ± 0.5 |
| Lung | 2.8 ± 0.1 | 3.5 ± 0.3 | 4.8 ± 0.8 | 3.1 ± 0.4 | 3.5 ± 0.1 | 4.1 ± 0.4 | 2.3 ± 0.3 |
| Liver | 4.0 ± 0.2 | 4.9 ± 0.1 | 4.7 ± 0.7 | 4.4 ± 0.5 | 4.9 ± 0.4 | 4.3 ± 0.6 | 3.8 ± 0.3 |
| Kidney | 26.6 ± 3.7 | 39.0 ± 3.2 | 30.4 ± 1.3 | 28.3 ± 2.4 | 35.9 ± 6.3 | 33.1 ± 4.5 | 27.8 ± 2.8 |
| Bladder | 130.6 ± 9.5 | 161.6 ± 21.0 | 90.0 ± 40.3 | 86.8 ± 44.3 | 144.4 ± 27.9 | 199.4 ± 46.4 | 191.2 ± 57.6 |
| Muscle | 1.8 ± 0.2 | 2.0 ± 0.3 | 2.0 ± 0.7 | 2.6 ± 0.2 | 3.2 ± 0.4 | 2.9 ± 0.1 | 0.8 ± 0.1 |
| Tumor | 12.8 ± 0.9 | 12.8 ± 2.4 | 10.7 ± 2.0 | 12.4 ± 1.5 | 9.7 ± 1.7 | 14.3 ± 2.9 | 9.0 ± 1.2 |
| Tumor/Heart | 1.9 ± 0.2 | 1.9 ± 0.6 | 1.3 ± 0.2 | 1.8 ± 0.2 | 1.7 ± 0.2 | 2.2 ± 0.3 | 1.4 ± 0.1 |
| Tumor/Muscle | 7.2 ± 0.3 | 6.4 ± 0.6 | 5.8 ± 1.1 | 4.7 ± 0.2 | 3.2 ± 0.7 | 4.8 ± 0.8 | 11.5 ± 2.6 |

Embodiment 9. Isolation, Purification and SPECT Imaging Scanning of Tc-99m Labeled Nanobody (1) 5.5 mg of $Na_2CO_3$, 15.2 mg of potassium sodium tartrate and 20.5 mg of $NaBH_4$ were added to 10 mL sterile bottle, respectively. CO was aerated, and 1 mL (35mCi) Na [99mTcO4] was then added. Bottle was sealed and left to react for 30 min at 80° C.

(2) 50 μL of antibody solution was added to 500 μL 99mTc $(CO)_3(H_2O)_3$ reaction solution (6.56mCi) to react for 90 min at 45-50° C.

(3) The 99mTc labeled nanobody was isolated with PD10 column and elute with 0.02 mol/L pH7.4 phosphate buffer solution. The radiochemical purity was identified by thin layer chromatography (TLC), (4) Estrogen tablets were implanted subcutaneously on the right back of NOD/SCID mice the day before cell inoculation. $1×10^7$ Her2 high expression tumor cells (BT474) were inoculated in right mammary fat pad. The tumor was used for experimental study when the size grown to 150-200 $mm^3$.

(5) Tumor-bearing mice were anesthetized with isoflurane. Tc-99m labeled nanobody (~10 ug, 5MBq) only or combined with 20× unlabeled nanobody was intravenously injected into the tail of the mice. Alternatively, 20× Trastuzumab or 20× Pertuzumab was intravenously injected into the tail for pretreatment 72 hours in advance.

(6) Scanning was performed 30 min after administration with acquisition method of static 15 min SPECT and medium resolution systemic CT.

Result showed that nanobody of invention could specifically accumulate in the tumor model with high HER2 expression, and did not compete with Trastuzumab or Pertuzumab. The Nanobodies of the invention could be used in Her2 targeted cancer diagnosis and curative effect evaluation as well as used for developing a new mechanism for Her2 targeted therapy.

Figure 7:
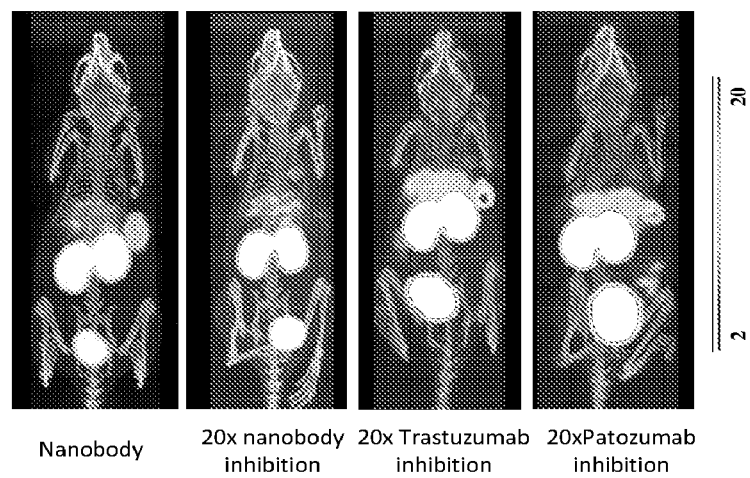
FIG. 7 shows SPECT-CT imaging results of 99m-Tc labeled Her2 nanobody in tumor-bearing mice with high expression of Her2. The nanobodies could specifically accumulate in the highly expressed tumor of Her2. Non-binding antibodies could be quickly removed from the blood through the kidney and bladder. Moreover, the nanobody did not compete with Trastuzumab or Patozumab.

The 30 min SPECT scan pictures and biodistribution data in vivo of some nanobodies in tumor-bearing mice were shown in FIG. 7 and Table 7.

TABLE 7

| Organ | ID %/g | | | |
|---|---|---|---|---|
| | Nanobody | 20× nanobody inhibition | 20× Trastuzumab inhibition | 20× Pertuzumab inhibition |
| Heart | 1.4 ± 0.6 | 1.6 ± 0.7 | 1.6 ± 0.2 | 2.2 ± 0.4 |
| Lungs | 2.6 ± 0.7 | 3.5 ± 3.2 | 3.0 ± 0.4 | 4.8 ± 1.2 |
| Liver | 4.8 ± 0.6 | 4.8 ± 0.2 | 7.4 ± 0.3 | 7.9 ± 0.5 |
| Kidney | 75.2 ± 8.3 | 65.0 ± 9.3 | 95.7 ± 4.0 | 81.6 ± 7.2 |
| Bladder | 41.8 ± 25.2 | 159.1 ± 62.0 | 20.5 ± 10.8 | 26.4 ± 12.5 |
| Muscle | 0.3 ± 0.1 | 0.5 ± 0.0 | 0.4 ± 0.1 | 0.3 ± 0.0 |
| Tumor | 8.9 ± 0.5 | 2.1 ± 0.8 | 9.7 ± 1.8 | 9.4 ± 1.2 |
| Tumor/Heart | 11.5 ± 4.5 | 2.5 ± 1.0 | 6.5 ± 1.6 | 4.3 ± 1.4 |
| Tumor/Muscle | 27.0 ± 7.6 | 4.1 ± 1.5 | 21.8 ± 5.6 | 28.6 ± 3.6 |

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

---

The invention claimed is:

1. A VHH chain of an anti-Her2 single domain antibody, the VHH chain comprising three complementary determining regions, CDR1, CDR2, and CDR3, wherein the three CDRs comprise the CDR1, CDR2 and CDR3 of any one of SEQ ID NOs.: 1-40.

2. A polynucleotide encoding the VHH chain of an anti-Her2 single domain antibody of claim 1.

3. An immunoconjugate comprising:
   (a) the VHH chain of an anti-Her2 single domain antibody of claim 1; and
   (b) a conjugating part selected from the group consisting of a detectable marker, drug, toxin, cytokine, radionuclide, enzyme, gold nanoparticle/nanorod, magnetic nanoparticle, viral coat protein or VLP, and a combination thereof.

4. The immunoconjugate of claim 3, wherein the radionuclide includes:
   (i) a diagnostic radioisotope selected from the group consisting of Tc-99m, Ga-68, F-18, I-123, I-125, I-131, In-111, Ga-67, Cu-64, Zr-89, C-11, Lu-177, Re-188, and a combination thereof; and/or
   (ii) a therapeutic radioisotope selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra-223, Ru-106, Na-24, Sr-89, Tb-149, Th-227, Xe-133 Yb-169, Yb-177, and a combination thereof.

5. The immunoconjugate of claim 3, wherein the drug is a cytotoxic drug.

6. The immunoconjugate of claim 5, where the cytotoxic drug is selected from the group consisting of:

antitubulin drug, DNA sulcus binding reagent, DNA replication inhibitor, alkylation reagent, antibiotic, folic acid antagonist, antimetabolic drug, chemosensitizer, topoisomerase inhibitor, *Catharanthus roseus* alkaloid and a combination thereof.

7. The immunoconjugate of claim 3, wherein the toxin is selected from the group consisting of:

an Auristatin, chlortetracycline, metotanol, ricin, ricin A chain, cobustatin, docamicin, adriamycin, daunorubicin, paclitaxel, cisplatin, cc 1065, ethidium bromide, mitomycin, etoposide, tenoposide, vincristine, vinblastine, colchicine, dihydroxyanthracnose diketone, actinomycin, diphtheria toxin, *Pseudomonas* exotoxin (PE) A, PE40, abrin, abrin A chain, modeccin A chain, gelonin, mitogellin, retstrictocin, phenomycin, enomycin, curicin, crotin, calicheamicins, *Sapaonaria officinalis* inhibitor, glucocorticoid and a combination thereof.

8. The immunoconjugate of claim 7, wherein the Auristatin is selected from the group consisting of Auristatin A, Auristatin F, MMAE and MMAF.

9. A detection reagent of Her2 protein or Her2 cancer, wherein the detection reagent comprises the immunoconjugate of claim 3 and a detection acceptable carrier.

10. The detection reagent of claim 9, wherein the detectable marker is one or more markers selected from the group consisting of isotope tracer, contrast agent, flow detection reagent, cellular immunofluorescence detection reagent, magnetic nanoparticles and imaging agent.

11. A pharmaceutical composition comprising:
(a) the VHH chain of an anti-Her2 single domain antibody of claim 1, or an immunoconjugate comprising the VHH chain of an anti-Her2 single domain antibody of claim 1; and
(b) a pharmaceutically acceptable carrier.

12. A method of treating a Her2 positive tumor in a subject, the method comprising administering an effective amount of the pharmaceutical composition of claim 11 to the subject.

* * * * *